United States Patent
Bake et al.

(10) Patent No.: US 9,826,993 B2
(45) Date of Patent: Nov. 28, 2017

(54) SURGICAL KIT FOR CARTILAGE REPAIR

(75) Inventors: Nina Bake, Lidingö (SE); Maria Kroll, Jönköping (SE); Niklas Johansson Herou, Bankeryd (SE)

(73) Assignee: EPISURF IP-MANAGEMENT AB, Stockholm (SE)

( * ) Notice: Subject to any disclaimer, the term of this patent is extended or adjusted under 35 U.S.C. 154(b) by 644 days.

(21) Appl. No.: 14/342,206

(22) PCT Filed: Aug. 31, 2012

(86) PCT No.: PCT/EP2012/067022
§ 371 (c)(1),
(2), (4) Date: Apr. 15, 2014

(87) PCT Pub. No.: WO2013/030370
PCT Pub. Date: Mar. 7, 2013

(65) Prior Publication Data
US 2014/0243836 A1     Aug. 28, 2014

Related U.S. Application Data

(60) Provisional application No. 61/530,497, filed on Sep. 2, 2011.

(30) Foreign Application Priority Data

Sep. 2, 2011 (EP) .................................. 11179923

(51) Int. Cl.
*A61B 17/17* (2006.01)
*A61F 2/30* (2006.01)
(Continued)

(52) U.S. Cl.
CPC .......... *A61B 17/1764* (2013.01); *A61B 17/17* (2013.01); *A61B 17/1739* (2013.01);
(Continued)

(58) Field of Classification Search
CPC ............ A61B 17/1764; A61B 17/1637; A61B 17/1675; A61B 17/1742; A61B 17/1746;
(Continued)

(56) References Cited

U.S. PATENT DOCUMENTS 5,520,692 A * 5/1996 Ferrante ............. A61B 17/1677
606/79
5,743,916 A * 4/1998 Greenberg ............. A61B 17/02
606/102

(Continued)

FOREIGN PATENT DOCUMENTS

CN     102083374     6/2011
EP     1698307 A1     9/2006
(Continued)

OTHER PUBLICATIONS

Office Action dated May 13, 2015 issued in corresponding European patent application No. 12 755 990.4 (6 pages).
(Continued)

*Primary Examiner* — Eric S Gibson
(74) *Attorney, Agent, or Firm* — Drinker Biddle & Reath LLP

(57) ABSTRACT

A guide tool adapted for removal of damage cartilage and bone and adapted for guiding insert tools during repair of diseased cartilage at an articulating surface of a joint is disclosed. The guide tool includes a guide base having a positioning body and a guide body protruding from the guide base. The guide body includes a height adjustment device and a guide channel with a length. The guide channel extends throughout the guide body and through the height adjustment device with one opening on a cartilage contact surface of the positioning body and one opening on the top of the height adjustment device. The guide body includes a height adjustment device being arranged to enable stepwise adjustment of the length.

11 Claims, 14 Drawing Sheets

(51) Int. Cl.
  *A61F 2/46* (2006.01)
  *A61F 2/38* (2006.01)
  *A61B 17/16* (2006.01)
  *A61B 17/00* (2006.01)
  *A61B 17/56* (2006.01)
  *A61B 90/00* (2016.01)
  *A61B 34/10* (2016.01)

(52) U.S. Cl.
  CPC ...... *A61F 2/30756* (2013.01); *A61F 2/30942* (2013.01); *A61F 2/3872* (2013.01); *A61F 2/4618* (2013.01); *A61F 2/4684* (2013.01); *A61B 17/1615* (2013.01); *A61B 17/1637* (2013.01); *A61B 17/1675* (2013.01); *A61B 2017/0046* (2013.01); *A61B 2017/568* (2013.01); *A61B 2034/108* (2016.02); *A61B 2090/034* (2016.02); *A61B 2090/036* (2016.02); *A61B 2090/037* (2016.02); *A61B 2090/062* (2016.02); *A61F 2002/30759* (2013.01); *A61F 2002/30948* (2013.01); *A61F 2002/4662* (2013.01); *A61F 2002/4687* (2013.01)

(58) Field of Classification Search
  CPC . A61B 17/175; A61B 17/1753; B23B 49/003; B23B 49/02; B23B 49/023; B23B 2260/048; B23B 2260/0482
  USPC ...... 606/88, 89, 96; 408/72 B, 115 B, 115 R
  See application file for complete search history.

(56) References Cited

U.S. PATENT DOCUMENTS

| | | | |
|---|---|---|---|
| 5,976,147 A * | 11/1999 | LaSalle | A61B 17/1604 606/102 |
| 6,063,091 A * | 5/2000 | Lombardo | A61B 17/1735 606/102 |
| 6,165,177 A | 12/2000 | Wilson et al. | |
| 6,306,142 B1 | 10/2001 | Johanson et al. | |
| 6,520,964 B2 | 2/2003 | Tallarida et al. | |
| 6,799,066 B2 | 9/2004 | Steines et al. | |
| 7,658,879 B2 * | 2/2010 | Solar | A61B 90/11 264/278 |
| 7,713,305 B2 | 5/2010 | Ek | |
| 1,753,365 A1 | 11/2010 | Sers | |
| 7,867,234 B2 * | 1/2011 | Collazo | A61B 17/1633 606/80 |
| 7,981,122 B2 * | 7/2011 | Labadie | A61B 90/11 248/168 |
| 8,062,302 B2 | 11/2011 | Lang et al. | |
| 8,066,708 B2 | 11/2011 | Lang et al. | |
| 8,083,745 B2 | 12/2011 | Lang et al. | |
| 8,105,330 B2 | 1/2012 | Fitz et al. | |
| 8,460,304 B2 | 6/2013 | Fitz et al. | |
| 8,641,721 B2 * | 2/2014 | Aram | A61B 17/1764 606/88 |
| 8,882,818 B1 | 11/2014 | Vestgaarden | |
| 9,009,012 B2 | 4/2015 | Bake et al. | |
| 9,216,089 B2 * | 12/2015 | Major | A61F 2/4684 |
| 9,254,196 B2 | 2/2016 | Bake et al. | |
| 9,386,999 B2 * | 7/2016 | Robertson | A61B 17/157 |
| 2002/0095214 A1 | 7/2002 | Hyde, Jr. | |
| 2002/0116006 A1 | 8/2002 | Cohen | |
| 2003/0100947 A1 | 5/2003 | Nadler et al. | |
| 2003/0216669 A1 | 11/2003 | Lang et al. | |
| 2004/0215203 A1 * | 10/2004 | Michelson | A61B 17/025 606/96 |
| 2005/0209694 A1 | 9/2005 | Loeb | |
| 2005/0234467 A1 * | 10/2005 | Rains | A61B 17/1735 606/96 |
| 2006/0198877 A1 | 9/2006 | Steinwachs et al. | |
| 2006/0235539 A1 | 10/2006 | Blunn et al. | |
| 2007/0021838 A1 | 1/2007 | Dugas et al. | |
| 2007/0100459 A1 | 5/2007 | Rhodes | |
| 2007/0233150 A1 * | 10/2007 | Blain | A61B 17/17 606/96 |
| 2008/0243127 A1 * | 10/2008 | Lang | A61B 5/4528 606/87 |
| 2009/0318927 A1 * | 12/2009 | Martin | A61B 17/1764 606/96 |
| 2010/0185201 A1 * | 7/2010 | Kim | A61C 1/12 606/80 |
| 2010/0234850 A1 * | 9/2010 | Dees, Jr. | A61B 17/155 606/87 |
| 2011/0054483 A1 * | 3/2011 | Howlett | A61B 17/1617 606/96 |
| 2011/0166661 A1 | 7/2011 | Boileau et al. | |
| 2011/0238071 A1 * | 9/2011 | Fernandez-Scoma | A61C 1/084 606/80 |
| 2012/0053588 A1 | 3/2012 | Lozier et al. | |
| 2012/0150030 A1 | 6/2012 | Reach, Jr. et al. | |
| 2012/0209394 A1 | 8/2012 | Bojarski et al. | |
| 2013/0172891 A1 * | 7/2013 | Bake | A61F 2/30756 606/80 |
| 2013/0173228 A1 * | 7/2013 | Bake | A61F 2/30756 703/1 |
| 2013/0185927 A1 * | 7/2013 | Bake | A61B 17/1675 29/592 |
| 2013/0211531 A1 | 8/2013 | Steines et al. | |
| 2014/0142643 A1 * | 5/2014 | Bake | A61B 17/1764 606/86 R |
| 2014/0224070 A1 | 8/2014 | Bake et al. | |
| 2014/0243836 A1 * | 8/2014 | Bake | A61F 2/30756 606/88 |
| 2014/0249781 A1 | 9/2014 | Bake et al. | |
| 2015/0190151 A1 * | 7/2015 | Budhabhatti | A61B 17/1666 606/96 |
| 2015/0320429 A1 * | 11/2015 | Katrana | A61B 17/846 606/96 |
| 2016/0089159 A1 * | 3/2016 | Ardito | A61B 17/1714 606/96 |
| 2016/0151076 A1 | 6/2016 | Bake et al. | |
| 2016/0199075 A1 * | 7/2016 | Bake | A61F 2/46 606/96 |

FOREIGN PATENT DOCUMENTS

| | | |
|---|---|---|
| EP | 1 753 365 A1 | 2/2007 |
| EP | 2138110 A2 | 12/2009 |
| EP | 2 389 905 A1 | 11/2011 |
| EP | 2685905 A1 | 1/2014 |
| JP | H10-504217 A | 4/1998 |
| WO | WO 96/24302 | 8/1996 |
| WO | WO-2006/091686 A2 | 8/2006 |
| WO | WO-2007/014164 A2 | 2/2007 |
| WO | WO-2008/098061 A2 | 8/2008 |
| WO | WO-2008/101090 A2 | 8/2008 |
| WO | WO 2008/138137 A1 | 11/2008 |
| WO | WO-2009/108591 A1 | 9/2009 |
| WO | WO-2009/111626 A2 | 9/2009 |
| WO | WO 2011/063257 A1 | 5/2011 |

OTHER PUBLICATIONS

Extended European Search Report dated Jun. 13, 2017 issued in corresponding European patent application No. 17155242.5 (7 pages).

* cited by examiner

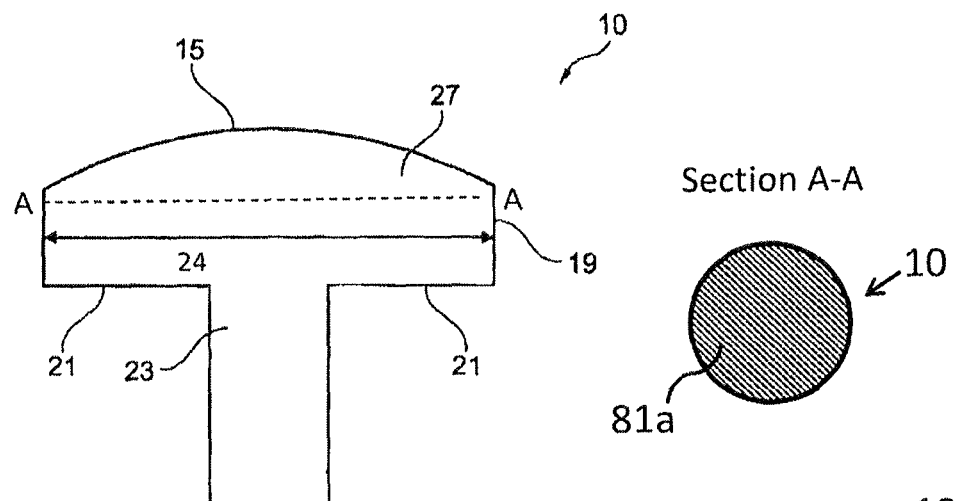
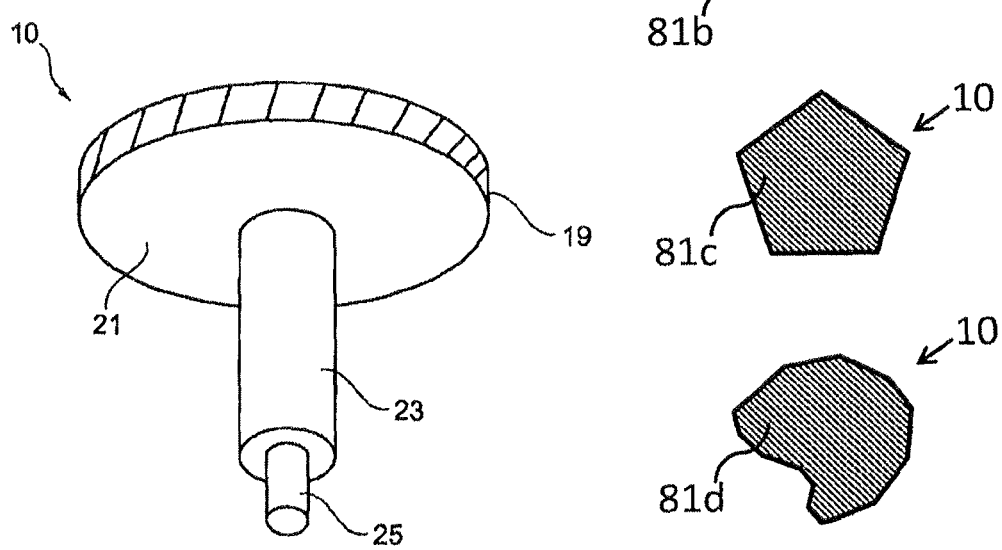
Fig. 3a
Fig. 3b
Fig. 3c

Section B-B

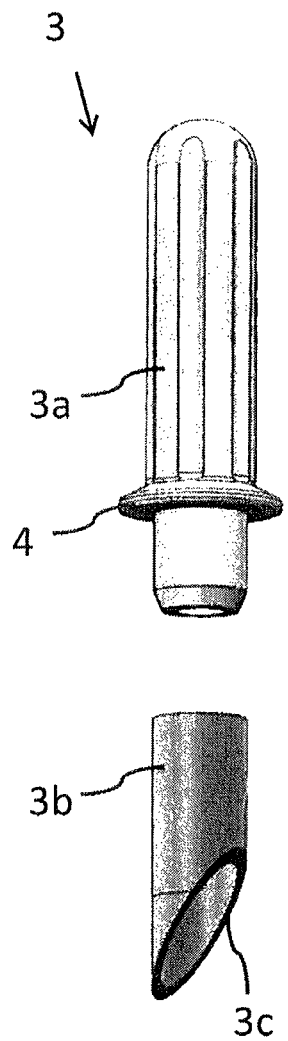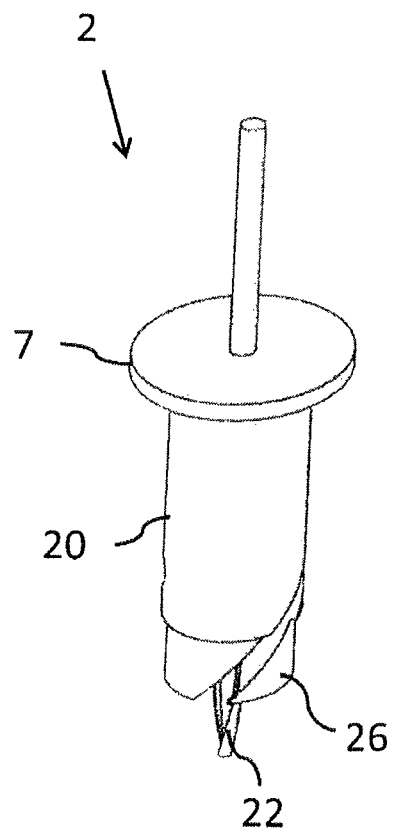
Fig. 9
Fig. 10

SURGICAL KIT FOR CARTILAGE REPAIR

CROSS-REFERENCE TO PRIOR APPLICATIONS

This application is a §371 National Stage Application of PCT International Application No. PCT/EP2012/067022 filed Aug. 31, 2012, which claims priority to European Patent Application No. 11179923.5 filed Sep. 2, 2011 and U.S. Provisional No. 61/530,497 filed Sep. 2, 2011, each of which are herein incorporated by reference in their entirety.

FIELD OF THE INVENTION

This invention relates in general to the field of orthopedic surgery tools and to surgery kits, kits of tools and medical implants. More particularly the present invention relates to a guide tool comprising a guide base and a guide body provided with a height adjustment device for use with a set of surgical tools. The guide tool is to be used for replacement or repair of damaged cartilage at an articular surface in a joint such as a knee, hip, toe or shoulder.

BACKGROUND

General Background

Pain and overuse disorders of the joints of the body are a common problem. For instance, one of the most important joints which are liable to wearing and disease is the knee. The knee provides support and mobility and is the largest and strongest joint in the body. Pain in the knee can be caused by for example injury, arthritis or infection. The weight-bearing and articulating surfaces of the knees, and of other joints, are covered with a layer of soft tissue that typically comprises a significant amount of hyaline cartilage. The friction between the cartilage and the surrounding parts of the joint is very low, which facilitates movement of the joints under high pressure. The cartilage is however prone to damage due to disease, injury or chronic wear. Moreover it does not readily heal after damages, as opposed to other connective tissue, and if healed the durable hyaline cartilage is often replaced by less durable fibrocartilage. This means that damages of the cartilage gradually become worse. Along with injury/disease comes a problem with pain which results in handicap and loss of function. It is therefore important to have efficient means and methods for repairing damaged cartilage in knee joints.

Today's knee prostheses are successful in relieving pain but there is a limit in the lifetime of the prostheses of 10-15 years. The surgical operation is demanding and the convalescence time is often around 6-12 months. In many cases today, surgery is avoided if training and painkillers can reduce the pain. Prostheses are therefore foremost for elderly patients in great pain, at the end of the disease process; a totally destroyed joint. There are different kinds of prostheses, such as half prosthesis, total prosthesis and revision knee, the latter used after a prosthesis failure. The materials used in today's knee prostheses are often a combination of a metal and a polymeric material, but other materials such as ceramics have also been used. The size of knee prostheses makes it necessary to insert them through open surgery.

Other attempts practiced at various clinics around the world with the main objective to repair or rebuild cartilage include biological approaches such as micro fractures, cartilage cell transplantation (ACI), periost flap, and mosaic plasty surgery. In mosaicplasty surgery grafts, in the form of plugs or dowels of healthy cartilage and underlying bone are harvested from nonbearing parts of the join i.e. areas of low stress in the joint. Such plugs may be denoted osteochondral plugs. In related surgical techniques similarly shaped plugs as those of mosaicplasty, but made of artificial material, may be used. The plugs or dowels are inserted into drill holes made at the diseased or damaged site, such that they form a mosaic pattern of healthy cartilage at the surface of the joint. Osteochondral autograft transfer (OATS) is a technique similar to mosaicplasty but during the OATS procedure the plugs are usually larger, and therefore only one or two plugs are needed to fill the area of cartilage damage. A difficulty with both mosaicplasty and OATS is to make sure that the plugs are inserted such that they form an even surface. If the plugs are offset from their intended position, e.g. such that they are tilted or projected over the surrounding cartilage tissue, they may cause increased wear and load on the joint, resulting in more pain for the patient. The biological treatments have shown only limited results this far, with implications such as high cost, risk of infection, risk of loosening, limited suitability for patients of different ages and the extent and location of damage. They do however have many advantages, especially for young patients who still are growing and who have better abilities for self-repair, if the mentioned difficulties can be overcome.

The advantages of implants have stimulated a further development of smaller implants that can be implanted with less invasive surgery. In this development there has also been an effort to achieve small joint implants, suitable for repair of a small cartilage injury that have a minimal influence on the surrounding parts of the joint. In the current development, such small implants are designed with an implant body that may be formed as a thin plate with a hard surface for facing the articulate side of the joint and a bone contacting surface for facing the bone below the damaged part of cartilage. The shape and the curvature of the articulate surface of the implant may be designed to be similar to the shape and the curvature of the part of the joint where the implant is inserted. Such implants are designed as mushrooms with an implant body or head and optionally with a peg or a rod projecting from the bone contacting side of the implant body for fastening the implant to the bone.

In the surgical operation of implanting small implants, including grafted plugs or artificial plugs used for mosaicplasty or OATS, it is critical that the implant is positioned in a precise manner. If the implant is offset from its intended position it may cause increased wear or load on the joint. For example, if the implant is tilted this may result in an edge that projects above the cartilage surface and causes wear on the opposing cartilage in the joint. Another example is when the implant is placed in a position with the surface of the implant projecting above the surface of the cartilage causing the joint to articulate in an uneven manner and increasing the load on an opposing point of the joint. For the patient, also small misplacements or deviations from an ideal position may result in pain, longer time for convalescence or even a surgical operation being done in vain and making it more difficult to repair the damage in the joint. A large burden is therefore placed on the surgeon not to misplace or misfit the implant. In order to support the surgeon during the implant surgery and to improve the positioning of the implant various tools and guides that support the surgical procedure have been developed.

Specific Background

Some of the surgical tools developed for implant surgery include guide tools having a channel or similar through which the surgical tools and/or the implant are guided throughout the surgery. There is a need for improved surgical tools which are easier to use and allows for more precision during surgery.

PRIOR ART

Examples of prior art disclosing smaller implants and tools for replacement of damaged cartilage are shown in:

WO2007/014164 A2 describes a kit comprising a plurality of small joint implants having different predetermined shapes described as circular, oval, L-shaped and triangular and tools for placing the implants and a method for placing the implant in a joint, e.g. in the knee or other joints where there is a need for repair of a cartilage and/or bone damage. In this piece of prior art each implant shape has a specific guide tool (1) which corresponds to the shape of the implant.

The cartilage damage is repaired by choosing the most suitable implant from the different shapes mentioned above. The corresponding guide tool (1) is selected and is used for faster reaming of the area where the implant is to be placed. A drill is used for drilling a hole to accept the post extending from the bone contacting side of the implant. Finally, the implant is placed on the area reamed or drilled out for the implant. Although it is the intention that the guide tool (1) shall be used for the preparation of the placement of the implant it is also said that the use of the guide tool (1) is optional, see passage sections [019, 020].

US20030216669 A1 describes methods and compositions for producing articular repair material used for repairing an articular surface. The method for designing an articular implant comprises; taking an image of the joint, reconstructing dimensions of the diseased cartilage surface to correspond to normal cartilage and designing the medical implant accordingly. This prior art also shows a surgical assistance device or surgical tool for preparing the joint to receive an implant. The surgical tool comprises one or more surfaces or members that conform to the shape of the articular surfaces of the joint. It can include apertures, slots and/or holes that can accommodate surgical instruments such as drills and saws. (see claim 18, [0029], [175] FIG. 13, 15, 16), and thus may also be designed and used to control drill alignment, depth and width, for example when preparing a site to receive an implant [0179]. The tool may be single-use or reusable [181]. These surgical tools (devices) can also be used to remove an area of diseased cartilage and underlying bone or an area slightly larger than the diseased cartilage and underlying bone [0182].

EP 1 698 307 A1 discloses an instrument for removing cartilage and introducing an implantable nonwowen into cartilage. The instrument may further comprise a cartilage puncher having a channel through which further instruments, such as surgical spoons or curettes, can be guided to the cartilage defect ([0028-0029]).

WO2008098061 A2 also describes examples of small articular surface implants and tools for placement of the implants. The tools and the implant are used to repair damaged articular cartilage areas.

WO2006091686 A2 describes a small implant for replacing a portion of an articular surface (see the abstract). The implant is placed using a rotating excision tool (see page 8 line 25) and the implant is selected from a set of predetermined sizes and shapes of implants ( WO 2009111626 describes implants for altering wear patterns of articular surfaces of joints (see [00190]) and a device and a method for repair of articular surfaces, in for example a knee. The implants and methods may replace all or a portion of the articular surface and achieve an anatomic or near anatomic fit with the surrounding structures and tissues, the techniques described herein allow for the customization of the implant to suit a particular subject, the implant is a mirror image of the articular surface, see [0057]-[0058]. The implants are selected from predetermined shaped and their location can be optimized for the patients wear pattern and the wear patterns are assessed by for example MRI [0061]-[0063], [0072]. The tools used for placement of the implants are selected depending on MRI images but not created depending on the images [00211].

WO2008101090 A2 describes a method for making a large implant suitable for a joint. The 3D surface of the joint implant is determined using MRI or CT depicting the damaged that is to be repaired.

US2006/0198877 A1 describes a medical instrument for autologous chondrocyte transplantation.

WO2009/108591 A1 describes a method and tools for repairing an articular cartilage defect and also an implant.

U.S. Pat. No. 6,306,142B1 describes a system and tools for transplanting a bone plug from a donor site to a recipient site.

US 2003/0100947 A1 describes a device for repairing articular cartilage defects.

OBJECT OF THE INVENTION

General Object

The general object of the invention is to solve the problem of providing means that aid the implantation of a cartilage replacement implant, including grafted or artificial plugs used for mosaicplasty or OATS, into the articular surface of a joint, aiding and facilitating the work for the surgeon and improving the positioning of the implant in order to generate optimal repair of damaged tissue and cause minimum damage to the surrounding tissue.

Partial Problems

The invention further seeks to solve the partial problems of facilitating inspection of the implantation site and removal of debris during surgery.

SUMMARY OF THE INVENTION

This invention relates in general to the field of orthopedic surgery tools and to surgery kits, kits of tools and medical implants. More particularly the present invention relates to a guide tool comprising a guide base and a guide body provided with a height adjustment device for use with a set of surgical tools. The guide tool is to be used for replacement or repair of damaged cartilage at an articular surface in a joint such as a knee, hip, toe or shoulder.

The present invention provides a guide tool (1) adapted for removal of damage cartilage and bone and adapted for guiding insert tools during repair of diseased cartilage at an articulating surface of a joint, wherein the guide tool (1) comprising;
a guide base (12) having a positioning body (11) and a guide body (13) protruding for said guide base (12);
characterized in
that the guide body (13) comprises a height adjustment device (16) and a guide channel (54) with a length (31) and wherein the guide channel (54) extends throughout the guide body (13) and through the height adjustment device (16) with one opening on a cartilage contact surface (50) of the positioning body (11) and one opening on the top of the height adjustment device (16); and wherein the guide body (13) comprises a height adjustment device (16) being arranged to enable stepwise adjustment of said length (31)

In another embodiment the guide tool (1) according to the invention comprises an height adjustment device (16) which comprises;

A guide tool (1) according to any of the preceding claims wherein the female receiving part 48 comprises an inner surface provided with a plurality of grooves 17 extending from the edge 113 of the upper opening of said female receiving part 48 a male part (47) equipped with ridges (105), protruding from an outer surface (106) of the male part (47)

Further varieties of the guide tool comprising any of the following optional, individual or combinable aspects; A guide tool (1) according to the invention wherein the guide body (13) the female receiving part (48), the male part (47) comprises a guide channel (54) and wherein the guide channel (54) has one opening on the cartilage contact surface of the positioning body (ii) and the other opening on top of the male part (47) of the height adjustment device and wherein the length (31) of the guide channel is adjusted by moving the male part in relation to the female receiving part so that a ridge (10)5 of the male part is moved from one groove (17) to another groove 17 of the female receiving part.

A guide tool (1) according to the invention wherein the stepwise height adjustment is made by steps of 0.01-0.4 mm or for example 0.1-0.3 mm or for example 0.2 mm due to the position of a groove (17) relative to the cartilage contact surface (50).

A guide tool (1) according the invention wherein the guide channel (54) having a cross-sectional profile that is designed to correspond to the cross-sectional profile (81) of an implant body (27, 627).

A guide tool (1) according to the invention wherein the cartilage contact surface (50) is designed to fit the contour of the cartilage or subchondral bone of an average patient or of a specific patient.

A guide tool (1) according to the invention, wherein the positioning body (11) is arranged with at least one breakage means (108) for enabling easy removal of part of the positioning body (11) by tearing, fracturing or similar breakage, such means (108) for example being provided by grooves, slots or perforations or other weakening of the structure.

A guide tool (1) according to the invention wherein the guide tool (1) (13) is also adapted for insertion of a medical implant (10), a grafted plug (boo) or an artificial plug having an implant body (27, 627) with a predetermined cross-sectional profile (81).

A guide tool (1) according to the invention wherein the male part (47) when placed inside the female part (48) is in a locked position and is not able to rotate due to the placement of the ridge (105) of the male part (47) in the groove (17) of the female receiving part (48).

A guide tool (1) according to the invention wherein the ridges (105) of the male part 47 is moved from one groove (17) to another by lifting the male part outwards from the cartilage surface and then placing the male part down in another groove (17), and wherein the male part (47) when placed inside the female receiving part (48) is in a locked position and is not able to rotate.

A guide tool (1) according the invention wherein the plurality of grooves 17 extending from the edge 113 of the upper opening of said female receiving part 48 and having a cross-section allowing the ridge to enter a groove 17 on the female receiving part 48 and stop against the abutment 114 of said groove 17.

A guide tool (1) according to the invention wherein the male part 47 has a cross-sectional profile that corresponds to the cross-sectional profile of a female part guide channel 120 with a tolerance enabling the insert tool to slide within the guide female part guide channel 120.

BRIEF DESCRIPTION OF THE FIGURES

The present invention will be further explained below with reference to the accompanying drawings, in which:

FIG. 3a-b shows an exemplifying embodiment of an implant to be used with the present invention. FIG. 3c shows exemplifying cross-sectional profiles of such implant.

FIG. 9 shows an exemplifying embodiment of a cartilage cutter according to the invention.

FIG. 10 shows an exemplifying embodiment of a drill and bone remover according to the present invention.

DETAILED DESCRIPTION OF THE INVENTION

Introduction

This invention concerns a guide tool (1) comprising a height adjustment device for use in orthopedic surgery. A surgical kit according to the invention further may comprise a set of tools for the implantation of an implant, or one or more grafted plugs or artificial plugs that replace damaged cartilage in a joint.

Figure 2:
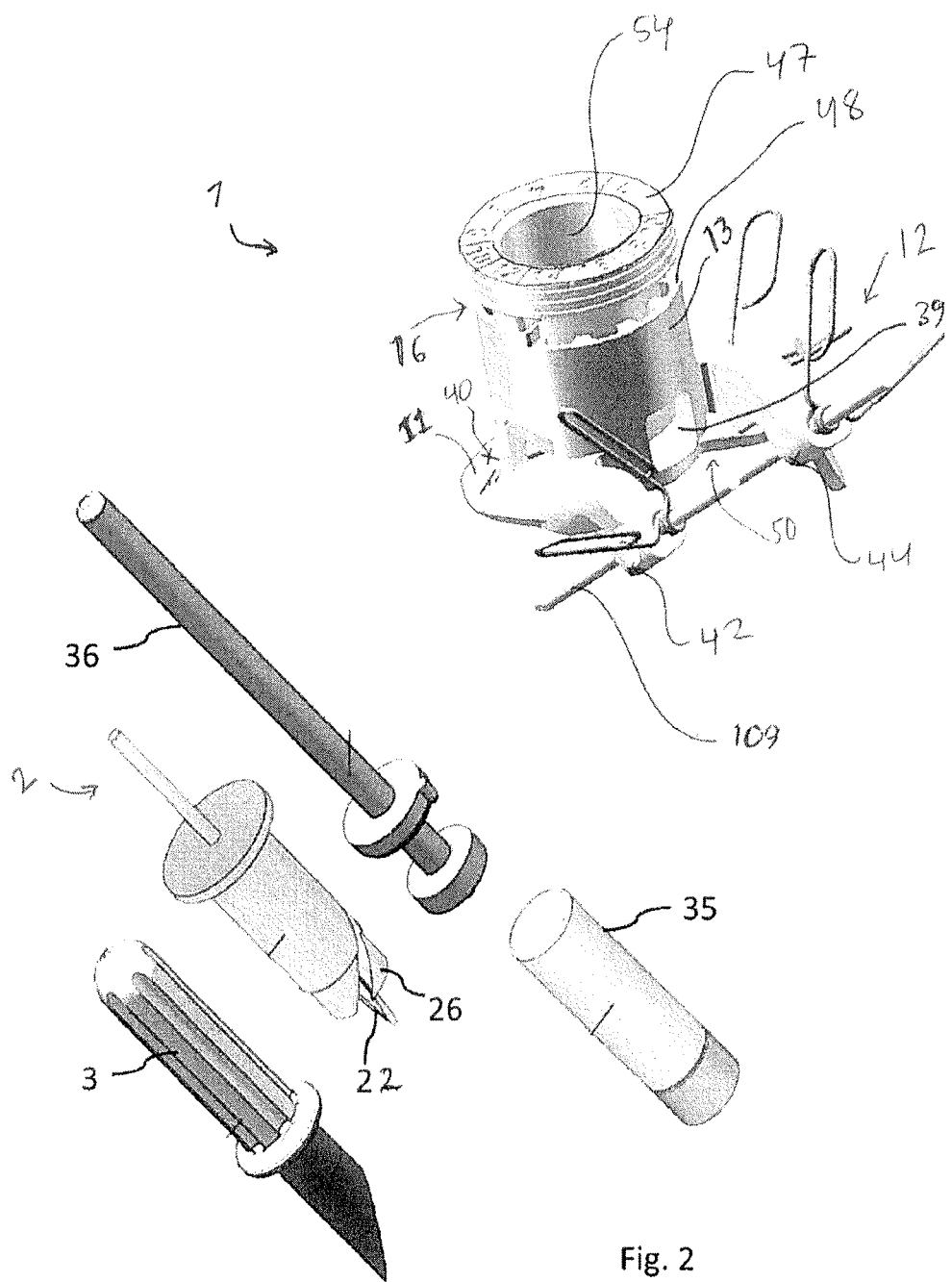
FIG. 2 shows a guide tool (1) according to one embodiment of the invention, exemplified by a guide tool (1) for a knee, the guide tool (1) comprising a guide base, a guide body comprising an height adjustment device and also a set of tools that may be used together with the guide tool (1) during surgery.

FIG. 2 shows a guide tool (1) according to one exemplified embodiment of the present invention, for use in repair of damaged cartilage in a knee joint. The guide tool (1) may be used together with tools that are adapted to an implant and to a joint; the guide also comprises a guide base 12 with a positioning body 11 and, a guide body 13. A height adjustment device 16 according to the invention comprises a male part 47 and a female receiving part 48 which when used together allows for stepwise adjustment of drill depth. The female receiving part 48 is fitted to the guide body 13 or is a part of the guide body. Further the surgical kit may comprise insert tools, for example a drill bit 2 and/or a bone remover 26, and or cartilage cutting tool 3 and/or an implant specific drill bit 2 or a drill and bone remover 2 and/or an implant dummy 36, and/or a dummy reference 37 and/or a mandrel 35. Optionally, the kit may also comprise the implant or one or more grafted plugs or artificial plugs to be implanted by use of the surgical kit.

The implant and the set of tools according to the invention are preferably individually designed for a person's joint. The implant and the set of tools are also optionally individually designed for a specific person's individual cartilage injury.

Exemplifying embodiments of the invention are shown herein which are especially adapted for cartilage replacement at the femur of a knee joint and at the joint of a toe. The invention may however, also have other useful applications, such as for cartilage replacement at an articulating surface at any other joint in the body, e.g. elbow, ankle, finger, hip and shoulder.

The Surgical Kit

This invention provides a guide tool (1) where the successful implant insertion is less depending on the skills of the surgeon compared to previously known methods and which facilitates inspection of the surgical procedure as well as removal of wear and debris during the surgery. This invention is preferably used together with individually designed insert tools and implant. Due to the design and the function of the guide tool (1) the surgical kit gives improved implantation precision and a precise desired placement of the implant in the joint every time. The precision of the surgery is "built in" into the design of the tools.

The guide tool (1) of the invention leads to shorter learning curves for the surgeon since the surgical kit facilitates for quick, precise, simple and reproducible surgery.

In one exemplifying embodiment the implant is intended for replacing damaged cartilage in a knee. The site where the implant is to be implanted according to the invention is an articular cartilage surface including, for example, the lateral femoral chondral (LFC) surfaces, medial femoral chondral (MFC) surfaces, trochlea surfaces, patella surfaces, tibia surfaces (e.g. surfaces of the tuberosities of the tibia), and combinations and portions thereof. For example implants may be placed on any one of these surfaces.

In another exemplifying embodiment the implant is intended for replacing damaged cartilage in a toe, for example on the cartilage surfaces between the metatarsals and the proximal phalanges bones in a toe.

In a further exemplifying embodiment the implant is intended for replacing damaged cartilage in a shoulder, for example on the articulation surfaces between the head of the humerus and the lateral scapula (specifically—the glenoid fossa of the scapula).

The implant is inserted through a small open surgery operation using a tool kit where the tools in the tool kits are preferably individually designed or tailor/custom made for the person who suffers from the injury. This leads to decreased suffering of the patient and is economically favorable since it leads to shorter convalescence time and less time for the patient at the hospital. By using this optionally individually designed surgery kit the implant insertion will be optimal and thus misalignment which is one of the problems associated with the common methods used today can be avoided.

Using the surgical kit according to the invention, small cartilage damages will require small implants and in this way combined with the design of the guide tool, a surgical operation with little tissue damage, a small open surgery, is needed for the person suffering from a knee injury. This gives the effect that minimal modifications on the underlying bone and surrounding tissue are required when preparing for the implant surgery. Using implants according to the present invention makes it possible to repair cartilage defects at a much earlier stage than previously. This early replacement of damaged cartilage may postpone or prevent osteoarthritis.

The object of the invention is to solve the problem of repairing damaged, injured or diseased cartilage in knees, toes, elbows or shoulders by providing an implant that will have better placement and thus a seamless placement in the cartilage.

The benefits from the implant according to the invention are relief from pain and swelling in the joint and also the restoration of a smooth, continuous articulating surface. The implant and the tool kit of the present invention also facilitates the return to normal activity with rapid recovery time and, possibility to postpone or avoid total knee replacement surgery. A less traumatic surgery procedure is used giving a potentially faster recovery after surgery.

Implants for Use with the Present Invention

The guide tool (1) of the present invention may be used for implantation of for example small implants and of bone and cartilage plugs, such as osteochondral plugs, or artificial plugs used in mosaicplasty or OATS. Examples of implants to be used with the guide tool (1) of the invention will be given below. The guide tool (1) may however be used with any implant having an implant body with a cross-sectional profile that corresponds to the cross-sectional profile the guide channel of the guide body 13 (see below).

Small Implant

FIG. 3a-3b shows an embodiment of a medical implant 10 that may be used with a surgical kit according to the present invention. The implant comprises an implant body 27 and an extending post 23. The implant body 27 has an articulate surface (first surface) 15 configured to face the articulating part of the joint and a bone contact surface (second surface) 21 configured to face bone structure in the joint. An extending post 23 extends from the bone contact surface 21. Between the articulate surface 15 and the bone contact surface 21 there is a cartilage contacting surface 19.

The implant may be specially designed, depending on the appearance of the knee and the shape of the damage and in order to resemble the body's own parts, having a surface which preferably corresponds to a three dimensional (3D) image of a simulated healthy cartilage surface. The implant can thus be tailor-made to fit each patient's damaged part of the joint. Alternatively, the implant to be used with the present invention may be of standard shapes and sizes.

Implant Body

Figure 13A:
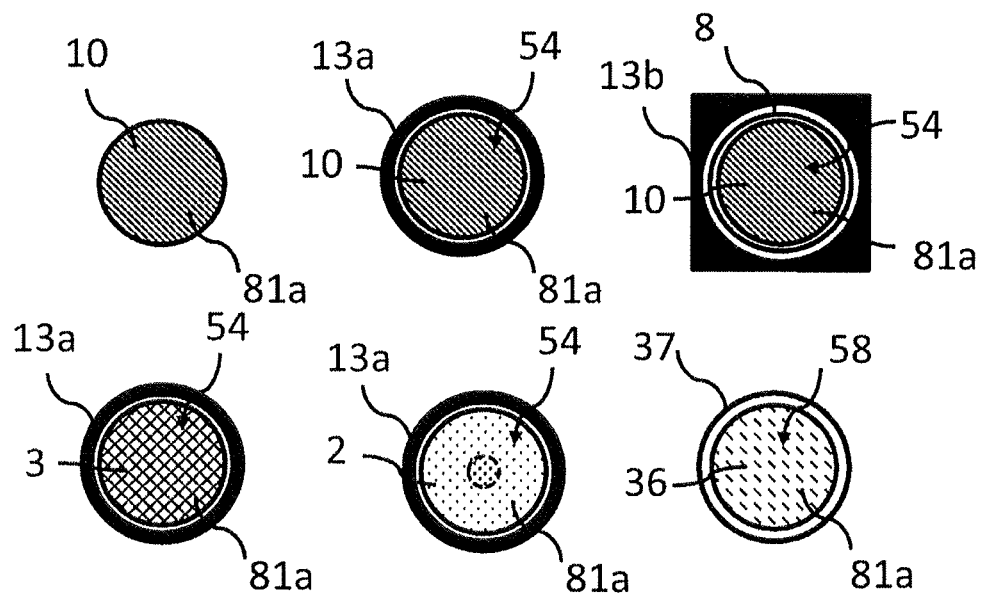
FIG. 13 shows exemplifying embodiments of the cross-sectional profiles of an implant and tools of the surgical kit according to the present invention.
Figure 13B:
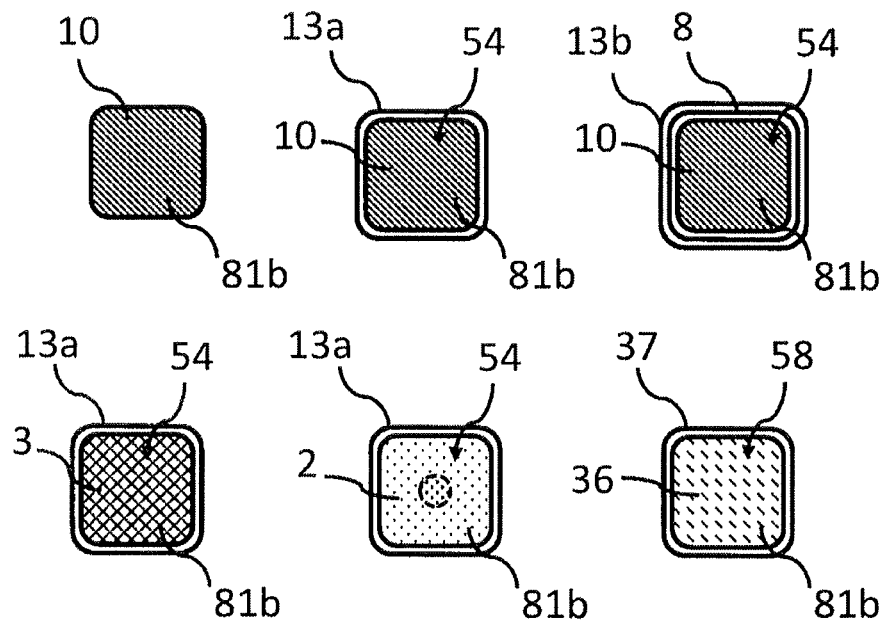

The implant body 27 is in one embodiment substantially plate shaped, meaning that the shortest distance (represented by 24 in FIG. 3a) crossing the surface 15 of the implant body 27 is substantially larger, e.g. at least 1.5 times larger than the thickness 14 of the implant body 27. By substantially plate shaped is meant that the implant body 27 may be substantially flat or may have some curvature, preferably a 3D curvature of the articulate surface 15. The plate shaped implant body 27 has a cross-section 81 that substantially corresponds to the area of the damaged cartilage, see FIGS. 3c and 13a-b implant 10, with four exemplifying cross-sectional views, 81a-d. The articulate surface 15 of the plate shaped implant body 27 may have a curvature that substantially corresponds to the curvature of a healthy articulating surface at the site of diseased cartilage. The curvature may for instance correspond to a simulated healthy cartilage reconstructed from an image taken with MRI image or the CT-scanning of the damaged cartilage surface of the joint. Once the implant 10 is placed in the joint there will be a surface with no parts of the implant pointing up from or down below the surrounding cartilage—the implant is thus incorporated to give a smooth surface.

The size and the shape of the implant body 27 may be individually adapted, or may be chosen from a set of standards, dependent on the size of cartilage damage and location of the cartilage damage. The area and shape of the implant can be decided by the surgeon himself or be chosen from predetermined shapes. For instance the cross-section of the implant body 27 may have a circular or roughly circular, oval, triangular, square or irregular shape, preferably a shape without sharp edges (see e.g. FIGS. 3c and 13a-b, implant 10). The size of the implant 10 may also vary. The area of the articulate surface 15 of the implant varies in different realizations of the invention between 0.5 cm$^2$ and 20 cm$^2$, between 0.5 cm$^2$ and 15 cm$^2$, between 0.5 cm$^2$ and 10 cm$^2$, between 1 cm$^2$ and 5 cm$^2$ or preferably between about 0.5 cm$^2$ and 5 cm$^2$.

In general, small implants are preferred since they have a smaller impact on the joint at the site of incision and are also more easily implanted using arthroscopy or smaller open surgical procedures. The primary factor for determining the size of the implant is however the nature of the lesion to be repaired.

The articulate surface 15 of the implant body 27, and the core of the implant body 27, comprises a biocompatible metal, metal alloy or ceramic. More specifically it can comprise any metal or metal alloy used for structural applications in the human or animal body, such as stainless steel, cobalt-based alloys, chrome-based alloys, titanium-based alloys, pure titanium, zirconium-based alloys, tantalum, niobium and precious metals and their alloys. If a ceramic is used as the biocompatible material, it can be a biocompatible ceramic such as aluminium oxide, silicon nitride or yttria-stabilized zirconia. Preferably the articulate surface 15 comprises a cobalt chrome alloy (CoCr) or stainless steel, diamond-like carbon or a ceramic. The articulate surface 15 and the core of the implant body 27 may comprise the same or different materials.

The articulate surface 15 may also be further surface treated in order to e.g. achieve an even more durable surface or a surface with a lower friction coefficient. Such treatments may include, for example, polishing, heat treatment, precipitation hardening or depositing a suitable surface coating.

The Bone Contact Surface

The implant body 27 has a bone contact surface (bone contact surface) 21, configured to face or contact the bone structure of the joint. In one embodiment the bone contact surface 21 comprises a biocompatible metal, metal alloy or ceramic, such as any of the metals, metal alloys or ceramic described above for the articulate surface 15. Preferably the bone contact surface 21 comprises a cobalt chrome alloy (CoCr), a titanium alloy, titanium or stainless steel.

In one embodiment the bone contact surface 21 comprises, or in one specific embodiment is coated with, a bioactive material. In an alternative embodiment of the invention the bone contact surface does not comprise a bioactive material and/or is uncoated.

The bioactive material of the bone contact surface, if present, preferably stimulates bone to grow into or onto the implant surface. Several bioactive materials that have a stimulating effect on bone growth are known and have been used to promote adherence between implants and bone. Examples of such prior art bioactive materials include bioactive glass, bioactive ceramics and biomolecules such as collagens, fibronectin, osteonectin and various growth factors. A commonly used bioactive material in the field of implant technology is the bioactive ceramic hydroxyapatite (HA), chemical formula $Ca_{10}(PO_4)_6(OH)_2$. HA is the major mineral constituent of bone and is able to slowly bond with bone in vivo. HA coatings have been developed for medical implants to promote bone attachment. Another bioactive material commonly used in prior art is bioactive glass. Bioactive glasses, generally comprising $SiO_2$, $CaSiO_3$, $P_2O_5$, $Na_2O$ and/or $CaO$ and possibly other metal oxides or fluorides, are able to stimulate bone growth faster than HA.

The bioactive materials described above have an anabolic effect on the bone i.e. stimulates bone growth. The fixation of the implant can also be improved by decreasing the catabolic processes i.e. decrease the amount of bone resorption next to the implant. The bone contact surface 21 and/or the extending post can also be modified with bisphosphonates. Bisphosphonates are substances that decrease the catabolic process of bone and binds readily to HA. One way to bind the bisphosphonate to the surface is by coating it with HA, which it readily binds to. The implant can also simply be immersed in a bisphosphonate solution or linked with some other biocompatible molecule e.g. carbodiimides, N-hydroxysuccinimide (NHS)-esters, fibrinogen, collagen etc.

In one embodiment the bone contact surface 21 is coated with a double coating. Such double coating may for instance comprise an inner coating comprising titanium (Ti). The second, outer coating, that is configured to contact the cartilage and or bone, is preferably a hydroxyapatite and/or beta tricalcium phosphate (TCP) coating containing more than 95% hydroxyl apatite or 95-99.5% hydroxyapatite. By this design even more long-term fixation of the implant is achieved, since bone in- or on-growth to the implant is further stimulated by the titanium, even if the more brittle hyroxyapatite would eventually shed/dissolve.

The bone contact surface may also be further modified with fluoro compounds or acid etching to enhance the bioactivity and the osseointegration of the surface. Another method to facilitate osseointegration is blasting of the bone contact surface.

The Extending Post

The implant replaces an area of damaged cartilage in an articulating surface of a joint. Before the implant is placed in the desired position, the damaged cartilage is removed and also a part of the bone beneath. Furthermore, a hole can be drilled to fit the implant structure. An extending post or rod-part 23 of the implant 10 (see FIG. 3), may be used for securing the implant 10 in the drilled hole of the bone. The length 900 of the extending post 23, extending from the bone contact surface 21, is adjusted to a length needed to secure the implant 10 in the bone. The extending post 23 is intended to give a primary fixation of the implant 10; it provides mechanical attachment of the implant 10 to the bone in immediate connection with the surgical operation.

The position of the extending post 23 on the bone contact surface 21 can be anywhere on the bone contact surface 21 or the extending post 23 may have a central position.

The extending post 23 has a physical structure in the form of for example a cylinder or other shapes such as one or more of a small screw, peg, keel, barb or the like.

The extending post 23 can in one embodiment of the invention be coated with a bioactive material, for example a bone stimulating material with single or double coatings and/or, a substance inhibiting bone resorption such as described for the bone contact surface 21 above. The surface of the extending post can also be further modified using e.g. fluoro compounds or acid etching or blasting, to enhance osseointegration of the surface.

In another embodiment of the invention the extending post 23 is uncoated and the extending post may comprise e.g. a metal, metal alloy or ceramic material, such as the metal, metal alloys or ceramic materials described for the articulate surface 15 above.

In one embodiment, as exemplified in FIG. 3a-b, the extending post 23 has a positioning part 25, where the positioning part 25 is located distal to the plate shaped implant body 27. The longitudinal symmetry axes of the first part of the extending post 23 and the positioning part 25 coincide. The diameter of the positioning part 25 is smaller than the diameter of the first part of the extending post 23.

Grafted Plug or Artificial Plug

Figure 4A:
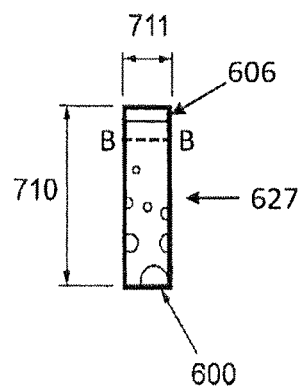
FIG. 4a-b shows an exemplifying embodiment of a grafted plug which may be used together with the present invention.
Figure 4D:
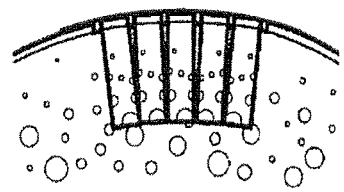
FIG. 4d-e show such grafted plugs implanted into bone by use of mosaicplasty surgery.

In an alternative embodiment the surgical kit of the present invention may be used for mosaicplasty or osteochondral autograft transfer (OATS). In such case the implant to be used with the surgical kit does not have a plate shaped implant body with extending post, but rather is a grafted plug taken from healthy bone and cartilage, see FIG. 4a-b, or an artificial plug, having the same general shape as a grafted plug but being made of an artificial material (see below). FIG. 4a shows a grafted plug 600 in the form of a bone and cartilage plug, such as a osteochondral plug, that has been harvested from a nonbearing part of a joint. The implant body 627 of the grafted plug 600 has a cylindrical to a substantially cylindrical form. By cylindrical to a substantially cylindrical forms meant a form or shape having parallel side walls, and having a cross-sectional profile 81 that is preferably circular or roughly circular but that may also have any other shape, including oval, triangular, square or irregular shape, preferably a shape without sharp edges, see exemplifying cross-sections 81a-d in FIG. 4c. At the upper part of the grafted plug 600 there is healthy cartilage 606 from the site of harvest, while the lower portion of the grafted plug 600 comprises bone tissue.

Figure 4B:
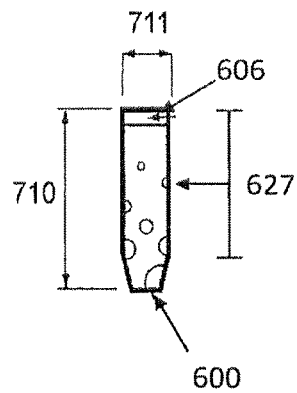

The grafted plug 600 may be further reshaped after harvesting by using a sharpener tool, see FIG. 4b. The sharpener tool may be constructed as a pencil sharpener, with a sharp blade, but which may be used to adjust the shape and/or the length of the bone part of the grafted plug 600, in order to arrange such that several plugs may fit together in an area of cartilage damage. The implant body 627, i.e. the upper part of the sharpened grafted plug 600, still has a cylindrical form, as defined above, i.e. with parallel side walls and a cross-sectional profile 81 that can have various shapes.

In another embodiment the plug used for mosaicplasty or OATS may be an artificial plug made of an artificial material such as synthetic polymer scaffolds, e.g. polylactide-co-glycolid, calcium sulfate, polycarbonate polyurethane or polyglycolide fibers or synthetic calcium. Such artificial plugs have the same geometrical shapes as the grafted plug 600 described above. Importantly for the present invention the artificial plug, like grafted plug 600, has an implant body 627 with a cylindrical form, that is a form or shape with parallel side walls and with a cross-sectional profile 81 that is preferably circular or roughly circular, but that may also have any other shape, including oval, triangular, square or irregular shape, preferably a shape without sharp edges.

A grafted plug 600 or an artificial plug, used with the present invention has a cross-sectional area that is between 0.5 cm$^2$ and 5 cm$^2$, between 0.5 cm$^2$ and 3 cm$^2$, or preferably between about 0.5 cm$^2$ and 2 cm$^2$ at its cylindrical portion. It has a length 710 that is between 1 and 4 cm, or between 1.5 and 3 cm. The cross-sectional diameter at the cylindrical portion may for example be 0.1-1 cm.

Figure 4E:
Figure 4C:
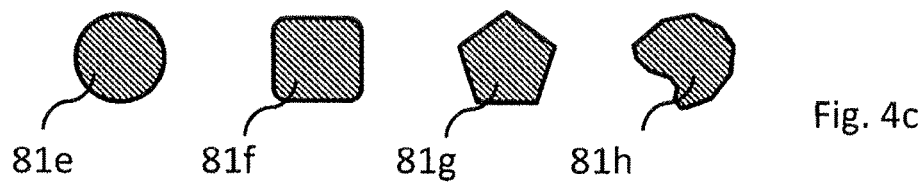
FIG. 4c shows exemplifying cross-sectional profiles of such grafted plug.

FIGS. 4d-e show a cartilage damage site repaired using mosaic repair technique, FIG. 4d from a cross-sectional side view of the joint, and FIG. 4e from above. Several grafted plugs 600 have been inserted at the site of damaged or diseased cartilage, to form a mosaic pattern. FIG. 4e also shows that grafted plugs 600 have been harvested from the healthy part of the joint (right hand side of the figure).

According to an embodiment of the present invention the amounts of plugs and also the size and shape of the healthy cartilage and bone plugs are selected depending on the shape and size of the injury.

The Set of Tools

Figure 5:
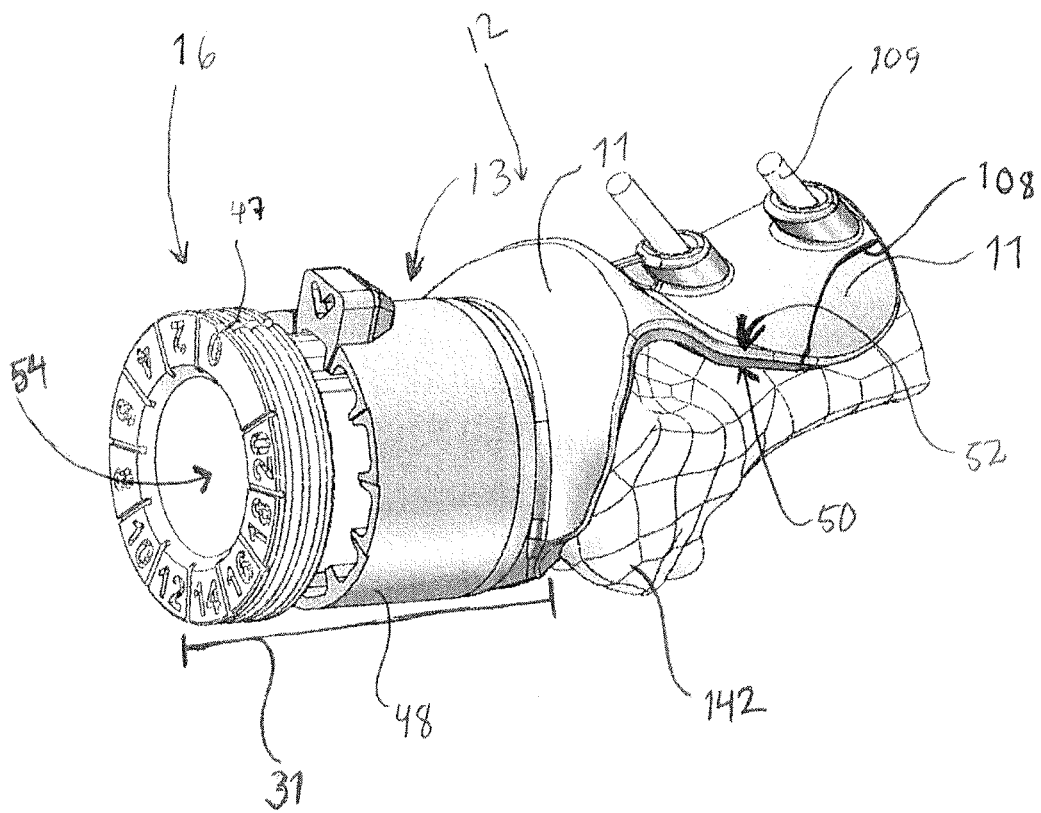
FIG. 5 shows an exemplified embodiment of the guide tool (1) according to the invention comprising a height adjustment device according to the invention placed on a toe joint.
Figure 6:
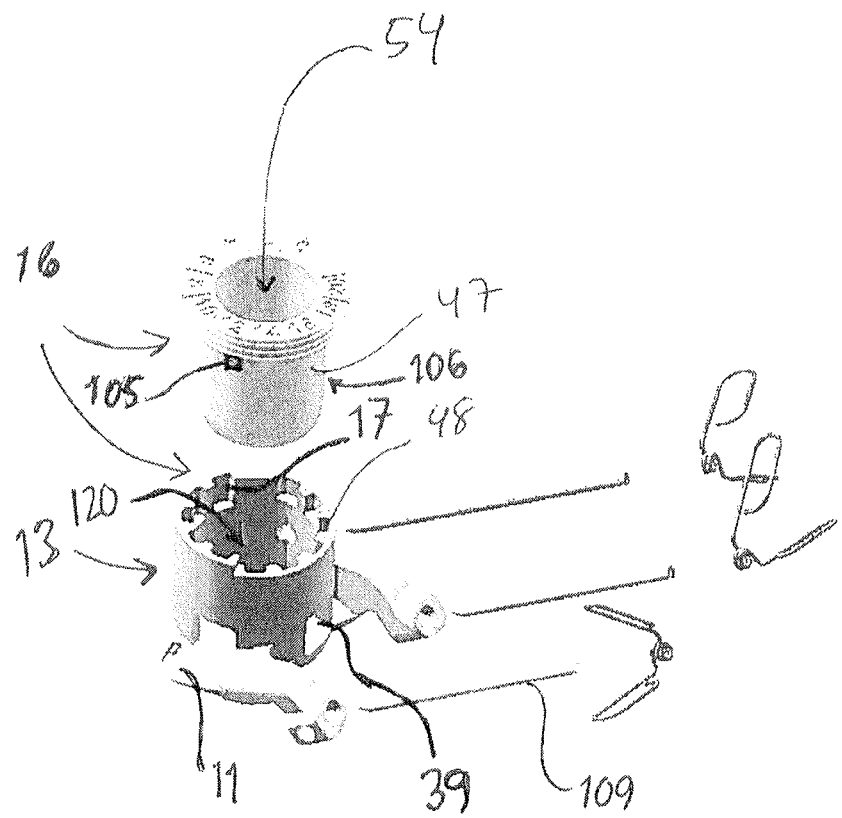
FIG. 6 shows an exemplifying embodiment of a guide tool (1) with a height adjustment device according to the present invention, showing the separate parts.
Figure 7:
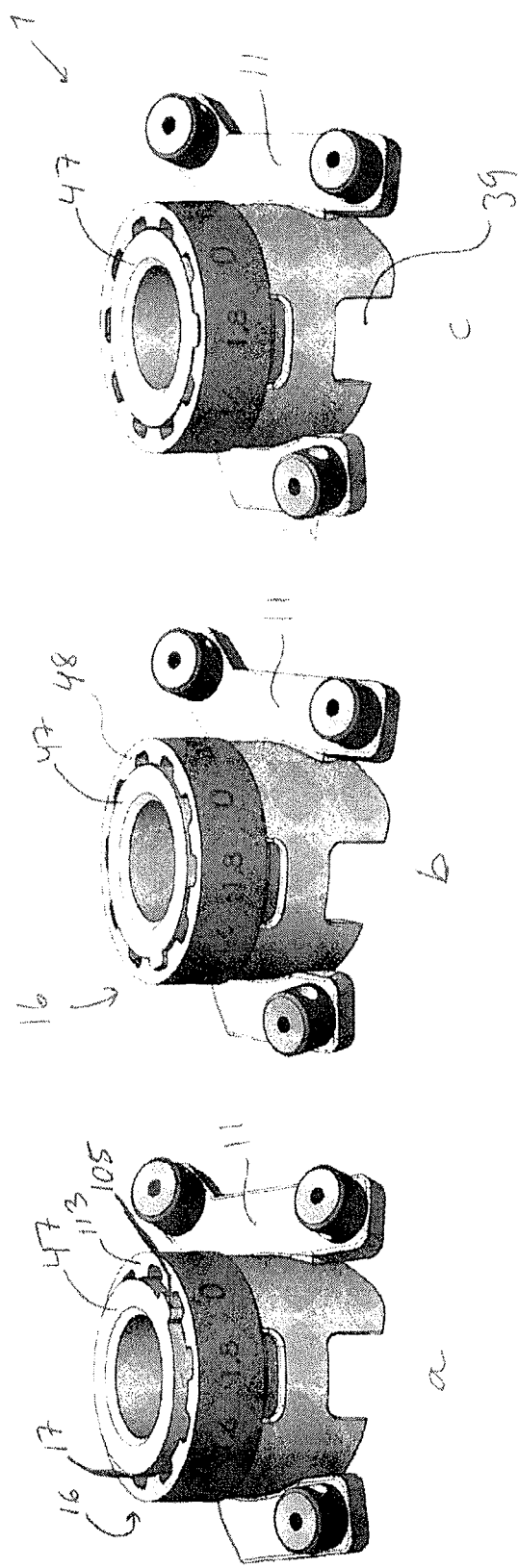
FIG. 7 shows exemplifying embodiments of the height adjustment device of the guide tool (1) according to the present invention.
Figure 8:
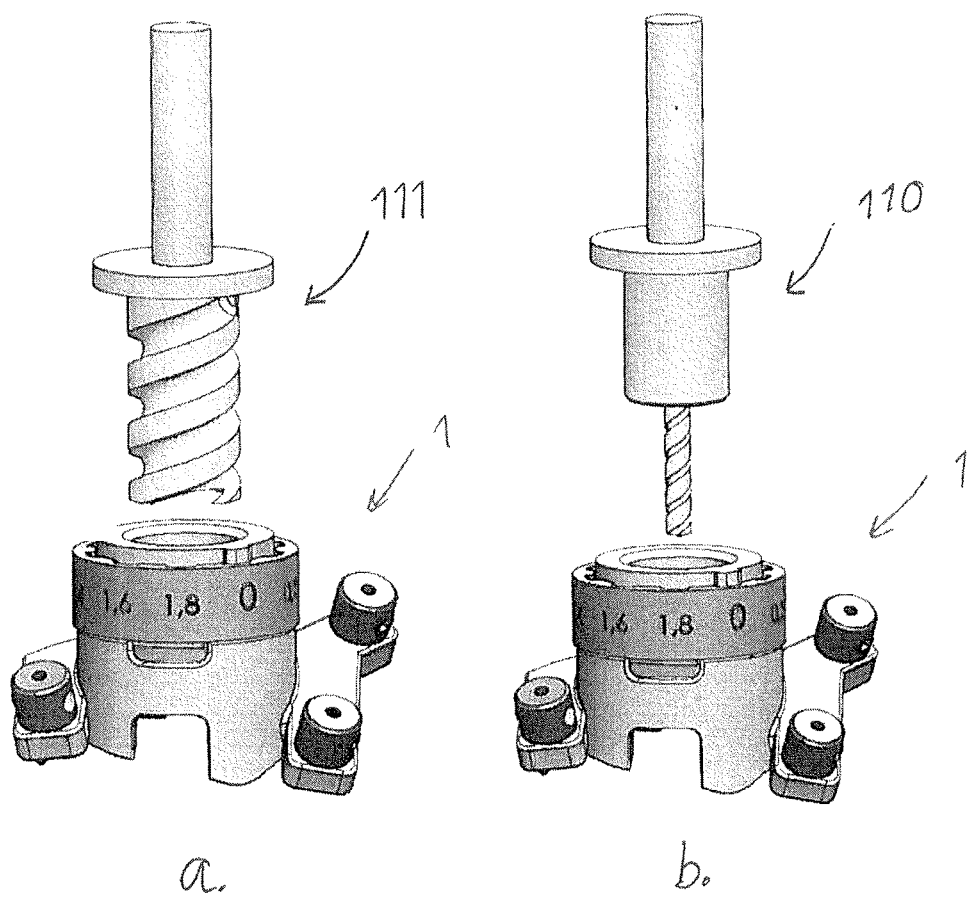
FIG. 8 shows an exemplifying embodiment of the use of the height adjustment device of the guide tool (1) according to the present invention together with a cartilage cutting tool 8a or a drill bit 8b.

The set of tools comprises a guide base 12, to which a guide body 13 with a guide channel 54 is attached, see FIGS. 5-7. It may also comprise a selection of insert tools, for use when mounting an implant 10, a grafted plug 600 or an artificial plug to the implant site, see FIGS. 2 and 8-11. The insert tools are in operation inserted in the guide channel 54 of the guide body 13 and fits in the guide channel 54, with a slight tolerance to allow a sliding movement of the insert tool in the guide channel 54. The cross-sectional profile, and thus the circumferential shape of the insert tools, corresponds to the chosen cross-section 81 of the implant body 27, 627 of the implant 10, grafted plug 600 or artificial plug, in size and shape (see FIG. 13a-b). The insert tools are in different embodiments of the invention provided in the form of for example a cartilage cutting tool, a punch, a drill, a drill guide, a bone cutting tool, a reamer guide and/or a hammer tool. Some insert tools are used together with further tools such as a drill bit and/or a reamer bit. An exemplifying set of insert tools will be described herein. The surgical kit of the invention may further be used with other insert tools, such as insert tools disclosed in PCT application PCT/EP2011/058473 or European patent application 11163405.1.

Guide Base, Guide Body and Guide Insert

FIGS. 5 and 6 shows an exemplifying embodiment of a guide tool of the invention, for use in a knee joint. FIG. 5 shows an exemplifying embodiment of a surgical kit of the invention, for use in a toe joint. The guide tool comprises a guide base 12 that is attached to a guide body 13 which further comprises a height adjustment device 16.

In FIG. 5 the guide base 12 is placed on the falangeal joint bone 142 of a toe respectively. The guide base 12 comprises a positioning body 11 and a guide channel 54, which may alternatively be denoted guide recess or guide opening or similar, through said positioning body 11 and guide body 13. The positioning body 11 has a cartilage contact surface 50 that has a shape and contour that is designed to correspond to and to fit the contour of the cartilage or the subchondral bone in the joint in a predetermined area surrounding the site of diseased cartilage. The cartilage contact surface 50 may be adapted to fit to the joint of an average patient or may be adapted, i.e. custom made, for an individual patient. The positioning body 11 also has a top surface 52 facing the opposite direction compared to the cartilage contacting surface 50.

In one embodiment the guide channel 54 has a cross-sectional profile that is designed to correspond to the cross-section 81 of the implant body 27, 627 of the implant 10, grafted plug boo or artificial plug to be implanted. In another embodiment the guide hole 53 has a cross-section that is slightly larger than the cross-section 81 of the implant body 27, 627. In a further embodiment the cross-sectional profile of the guide hole 53 need not correspond to the cross-section 81 of the implant body 27, 627. Where the cross-sectional profile of the guide hole 53 is different from the cross-section 81 of the implant body 27, 627, correspondence or matching to the cross-section 81 of the implant body 27, 627 is provided by the cross-sectional profile of the guide channel 54 of the guide body 13 only (see below).

An embodiment of a guide body 13 is shown in FIGS. 5 and 6. The guide body 13 has a guide channel 54 that extends through the guide body 13. The outer shape and design of the guide body 13 may vary, as is schematically illustrated by a circular design 13a and a square design 13b in the top row of FIG. 13a (implant 10 and guide body 13a, 13b seen from above). The guide channel 54 of the guide body 13, however, has an inner cross-sectional profile (see FIG. 13a-b) that is designed to correspond to the cross-section 81 of the implant body 27, 627. In other words, the implant body 27, 627 fits the guide channel 54, with a slight tolerance to allow a sliding movement of the implant in the guide channel 54.

In an alternative embodiment the guide body 13 has a guide channel that has a cross-sectional profile which is larger than the cross-sectional profile 81 of the implant body 27, 627. In this case the guide channel 54 that is designed to correspond to the cross-section 81 of the implant body 27, 627 is instead provided by a guide insert 8 (see FIGS. 6 and 7, and top view in FIG. 13a-b). The guide insert 8 is designed to have outer proportions to make it fit into the guide channel of the guide body 13. Its guide channel 54 is designed to have an inner cross-sectional profile that corresponds to the cross-section 81 of the implant body 27, 627. In other words, the implant body 27, 627 fits the guide channel 54, with a slight tolerance to allow a sliding movement of the implant in the guide channel 54. In this way the guide insert 8 works as an adapter, such that a guide body 13 with a guide channel of a certain size might be used for implantation of implants of various sizes, by use of guide inserts 8 with varying guide channels 54 that fit implants of corresponding varying sizes.

The height 31 of the guide channel 54 must be sufficiently long to give support to the tools used inside the guide body 13. The height 31 of the guide channel 54 is preferably also sufficiently high to be easily accessible for the surgeon during surgery. In one embodiment, the top of the guide channel 54 is designed to project above the tissue surrounding the surgery cut when the guide tool (i) is placed on the cartilage in a joint during surgery. The height 31 is preferably higher than the thickness of the surrounding tissue. In this way, the opening of the guide channel 54 is easy to access for the surgeon. The height 31 of the guide channel 54 is between 1 and 10 cm, preferably 3-10 cm and always sufficiently high to ensure stabilization of the tools that are to be inserted into the guide channel 54.

In other embodiments the guide tool (1) according to the invention may be used in mosaicplasty or OATS surgery. The guide body 13 in such alternative embodiment may comprise at least two guide channels 54. Each of the guide channels 54 is designed to have a cross-sectional profile that corresponds the cross-section 81 of an implant body 627 of a grafted plug 600 or an artificial plug. The at least two guide channels 54 may have cross-sectional profiles that are identical. Alternatively their cross-sectional profiles may be different in shape and/or size/area, depending on the cross-sectional profile 81 of the respective grafted plugs 600 or artificial plugs, that are to be implanted. Each of the guide channels 54 may also be arranged in the guide body 13 at different angles, depending on the angle in which the respective plugs are to be implanted.

The positioning body 11 may be provided with an inspection window 39, i.e. a window or hole through the side of the positioning body 11, into the guide channel 54, see FIGS. 6 and 7. The inspection window 39 facilitates inspection of the site of implantation during surgery, also when the guide body 13 is attached to the guide base 12, see FIGS. 2 and 7.

The guide base 12 is easy to place due to the precise fit of the positioning body 11 on the cartilage surface. The guide base 12 is designed to be inserted in a lesion which is as small as possible to be able to repair the specific cartilage damage. The size and shape of cartilage contact surface 50 of the guide base 12 is determined depending on the size and shape of the damaged cartilage and also depending on the position of the cartilage damage in the joint. The size and shape of the surface 50 and the positioning body 12 is a consideration between the following aspects; minimize surgery lesion, maximize stability for the guide base 12, anatomic limitations on the site of the injury, and that not all cartilage surfaces in a joint can be used for placement of the guide tool. A large spread of the cartilage contact surface 50 is to prefer to get good stability of the guide tool, however, a large surface area of the surface 50 may also lead to a large surgical intervention and this is undesired. Thus the size of the cartilage contact surface 50 and of the positioning body is determined by a balance between the desire to achieve good positioning stability and small surgical operations. Also, the cartilage contact surface 50 does not need to have a continuous, regular shape, but may have an irregular shape, as long as it gives adequate support and stable positioning of the guide base 12.

When designing the guide tool, the cartilage contact surface 50 can be designed to cover three points (see FIG. 2, points 40, 42, 44 for an example) distributed over the cartilage surface of the joint where the implant is to be inserted. The points are chosen to give maximum support and positional stability for the positioning body 11 and thus these points, either decided and identified by the surgeon or automatically identified by design software, serve as the ground when designing the surface 50 of the guide base 12. The cartilage contact surface 50 can also be formed such that it uses the curvature in the cartilage surface in a joint for stability. For example, in a knee joint, the condyles are separated from each other by a shallow depression, the posterior intercondyloid fossa, this curvature together with the medial epicondyle surface can be used to give the cartilage contact surface 50 a stabile attachment to the cartilage surface in a knee joint. The surface is in one embodiment a continuous surface covering a selected area surrounding the cartilage damage. In another embodiment the cartilage contact surface is distributed over a plurality of points, preferably three or more of separated contact points. The cartilage contact surface does not need to be a continuous, regular surface, but preferably has at least three points exemplified by 40, 42 and 44 for stability.

Optionally the cartilage contacting surface 50 can be further stabilized by attachment with nails, rivets 109 or similar attachment means 48 to the bone surrounding the cartilage in a joint (see FIG. 2). This additional attachment with rivets 109 or the like gives additional support and stability and also gives the possibility to keep the cartilage contact surface as small as possible. The position of the rivets may be predetermined and marked out on the surface 50 by premade drill holes.

As stated above, the size and shape of the positioning body 11 of the guide base 12 is determined in order to minimize the surgical intervention while also maximizing the stability of the guide base 12 in the joint. While designing the guide base 12, e.g. by use of X-ray, MR or CT images from the patient it is normally desired to have a positioning body that is as large as possible, in order to ensure maximum stability and proper positioning of the guide base 12 in the joint. However, not all facts on the patient's joint may be known through the X-ray, MR or CT images, and thus the surgeon may want to adjust the positioning body it during surgery. For example, osteophytes might have formed in the joint and are often difficult to identify in the imaging procedures. Also, the surgeon might find during surgery that the shape of the guide base 12 requires an unnecessarily large incision to be able to insert the guide base 12 into the joint. In order to facilitate adaptation of the size and shape of the guide base 12 during surgery, the positioning body may be arranged with breakage means 108 that enable easy removal of part(s) of the positioning body 11 by tearing, fracturing or similar ways of breakage, see e.g. FIG. 5. Such breakage means may for example be provided through grooves, slots or perforations or other weakening of the positioning body 11 structure.

The guide base 12 with guide body 13 aid with exact precision removal of a volume of cartilage and subchondral bone and also guide the placement of the implant 10, the grafted plug boo or the artificial plug in for example a knee. The guide base 12 is placed on the cartilage surface of a knee or a toe, see for example FIG. 2 or FIG. 5, during surgery.

The guide base 12 and the guide body 13 are manufactured using suitable materials that are approved for use in medical procedures, e.g. a ceramic, plastic, metal, metal alloy or alumina material, or a combination. The guide base 12, especially the cartilage contact surface 50, is also preferably made of a material that is smooth, even and/or has low friction, in order to lessen the risk of wear and damage to the cartilage on which it is to be placed. Such materials include e.g. metals ceramics and polymers such as acrylonitrile butadiene styrene (ABS). The used materials may further be polished. The guide base 12 is for example made of a plastic material, such as polyamide or epoxy, while the guide body 13 may be made of the same material as the guide base 12 or is made of a metal material or stainless. The plastic material of the guide base 12 and the guide body 13 is easy to manufacture, e.g. using selective laser sintering (SLS) or stereolithography (SLA) technologies, also when adapted for a specific patient. It is also gentle to the cartilage surface of the joint. The us of metallic material when manufacturing the guide body 13 on the other hand, provides a wear resistant material that is to be in contact with the insert tools, thus minimizing the risk of generating wear debris from the guide body for example during drilling. It is also autoclavable and thus reusable. In one embodiment the guide base 12 is adapted to a specific patient, by having a cartilage contact surface 50 and a positioning body 11 that are designed to match the cartilage surface and the shape of the joint of the patient. In one embodiment the guide body 13 is made in a number of standard shapes and sizes, matching corresponding shapes and sizes of a set of standard implants 10, while in another embodiment the guide body 13, as well as the implant 10, is also adapted to the specific patient.

Height Adjustment Device

Figure 16:
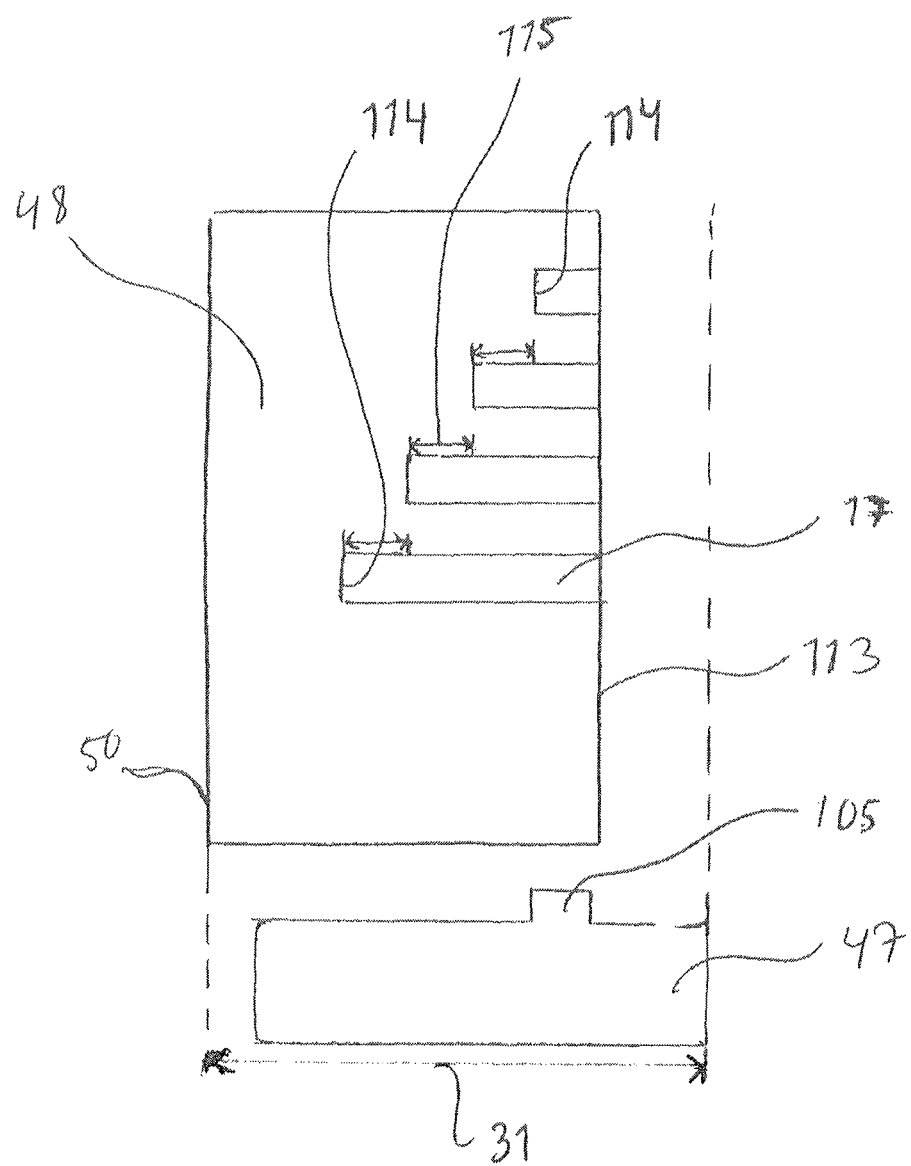
FIG. 16 shows for the purpose to illustrate the inner surface of the female receiving part rolled out in a plane with the male part below.

In FIG. 16 is illustrated that the inner surface of the female receiving part 48 is provided with a plurality of grooves 17 extending from the edge 113 of the upper opening of said female receiving part 48. FIG. 16 shows for the purpose of illustration the inner surface of the female receiving part 48 rolled out in a plane with the male part 47 placed beneath.

The grooves 17 extend from the upper opening edge and ends in an abutment 114 at a predetermined distance from the edge.

The male part 47 is provided with a ridge 105 protruding from the envelope surface of the male part 47 and having a cross-section allowing the ridge to enter the grooves 17 on the 20 female receiving part 48 and stop against the abutment of said grooves 17.

The male part is in the outermost position in a zero-mode and may from there be adjusted inwards allowing the surgeon stepwise the for example make stepwise deeper drillholes.

In a preferred embodiment the surgical kit further comprises a height adjustment device 16 as for example illustrated in FIGS. 2, and 5 and 6 and 16. The height adjustment device 16 of the embodiment shown is comprised by two parts, a female receiving part 48 and a male part 47. The female receiving part 48 of the height adjustment device may be arranged as a part of the top of the guide body 13 or fitted to the guide body 13. The height adjustment device 16 is further arranged such that it may be used to adjust the length 31 of the guide channel 54, see FIG. 5. The length 31 of the guide channel 54 determines the depth of drilling and cutting of the bone in the joint, as will be described further below. Thus, by being able to adjust the length 31 of the guide channel the surgeon is also able to adjust the depth of drilling and cutting into the bone. The length 31 of the guide channel may be varied since the guide body 13 and the height adjustment device 16 parts are able to move in relation to one another. Further, the male part 47 and the female receiving part 48 of the height adjustment device may be arranged such that the length 31 of the guide channel may be varied at certain stepwise intervals 115, e.g. at 200 µm or at 100-300 µm intervals or steps, or any other desired interval, see for example FIG. 16. For example the height might be adjusted between for example 0.2-3 mm, in one or several steps. This may for instance be achieved by arranging the male part 47 inside the female receiving part 48 of the height adjustment device 16 such that the male part 47 insert tool to have a cross-sectional profile that corresponds to the cross-sectional profile of the female part guide channel 120 with a tolerance enabling the insert tool to slide within the guide female part guide channel 120. For example, the construction may be arranged such that the guide body 13 and height adjustment device 16 may be turned in relation to one another at preset steps, by lifting the male part sot that the protruding ridges may slip out of one groove and enter another groove. When the male part 47 is fitted in the female part their position are locked in relation to each other or prone to hook each other at those intervals. The female part comprises grooves or ledges 17 at different heights relative to the positioning body of the guide tool. The male part 47 comprises a guide channel 54 inside the male part 47, the guide channel 54 may be cylinder shaped and protruding ridges 105 on the outer surface of the male part 47. When the male part 47 is placed inside the female receiving part 48 the protruding ridges 105 of the male part 47 are placed or located inside one of the grooves 17 on the female receiving part 48. The position of the grooves 17 and the position of the ridges 105 in relation to the positioning body or the cartilage contact surface 50 adjust or regulate the length 31 of the guide body 13. The height adjustment device 16 may be used by the surgeon to adjust the depth of drilling, e.g. by increasing the drill depth in steps at the preset intervals. The height adjustment device 16 may advantageously be used together with an implant dummy 36, as described below, to make sure that the drill depth in the bone matches the height 14 of the implant body 27. This ensures that the articulate surface 15 of the implant 10 will be in line with the surrounding cartilage at the site of implantation once implanted. For further description of how the height adjustment device 16 is used during surgery, see below in connection with FIGS. 14a-b.

Cartilage Cutting Tool

The cartilage cutting tool 3 is a tool which in an alternative embodiment may be used to cut the cartilage in the joint around the area of damaged cartilage to prepare for the insertion of the implant. The cartilage cutting tool may for example be a cartilage cutter 3, as shown in FIGS. 2 and 9, a punch or a drill and bone remover 2. It is used inside the guide channel 54 of the guide body 13 and fits in the guide channel 54, with a slight tolerance to allow a sliding movement of the cartilage cutting tool 3 in the guide channel 54 (see FIG. 13a-b). The cartilage cutting tool 3 preferably cuts the cartilage so that the cut edges of the cartilage are sharp and smooth. These sharp and smooth edges are of great importance when the implant is placed into the prepared recess in the cartilage and bone. A hole in the cartilage which is cut (or punched or drilled) with the cartilage cutting tool 3 according to the invention ends up with a precise fit of the implant into the prepared cartilage since the cartilage cutting tool allows for an exact, precise cut. The recess in the cartilage, made by the cartilage cutting tool 3 always corresponds to the chosen cross-section 81 of the implant body 27 in size and shape.

In one exemplifying embodiment of the invention the cartilage cutting tool is a cartilage cutter 3. The cartilage cutter 3 is used to cut the cartilage in the joint around the area of damaged cartilage to prepare for the insertion of the implant with a cutting technique.

The cartilage cutter 3 has a handle 3a, a cartilage cutter body 3b and a cutting blade with sharp cutting edges 3c. The cartilage cutter body 3b has a cross-sectional profile that is designed to correspond to the inner cross-sectional profile of the guide channel 54 with a tolerance enabling the cartilage cutter body 3b to slide within the guide channel 54 (see FIG. 13a-b). Also, the cross-sectional profile is designed to correspond to the cross-section of the implant. Thus, the cartilage cutter body 3b fits the inside of the guide channel 54, see FIG. 13, with a slight tolerance to allow a sliding movement of the cartilage cutter in the guide channel 54. The fit ensures the correct, desired placement of the cartilage cutting edges 3c on the cartilage surface and thus the precise removal of the damaged cartilage area.

The cartilage cutter 3 of the embodiment shown in FIG. 9 has a cartilage cutter body 3b comprising a circular cutting blade that has been cut at an angle that is not perpendicular to the length of the cutter body 3b. This creates an oval cutting edge 3c with a pointy appearance, further increasing the sharpness of the cartilage cutter 3. The cutting edge 3c is arranged to cut the cartilage in a shape corresponding to the cross-sectional profile 81 of the implant body 27.

The material of the cartilage cutter body 3b is chosen from materials which can give the cartilage cutter 3 sharp cutting edges 3c. The material also needs to be stable in order to withstand the pressure when the cartilage cutter 3 is pushed into the cartilage. Examples of such materials are metals such as stainless steel or ceramic material or a plastic material or a hard coated material, preferably stainless steel.

The cutter body 3b may be permanently attached to the handle 3a, or may, more preferably, be removable attached to the handle 3a, such that the handle 3a is reusable while the cutter body 3b is be exchangeable (see FIG. 9).

The cartilage cutter 3 may be provided with a safety stop 4. The safety stop 4 has a cross-sectional profile that is larger than the gross sectional profile of the guide channel 54. In case the cutter would risk digging too deep into the bone the safety stop 4 will be stopped against the top of the guide body 13 and/or height adjustment device 16, thus preventing the cartilage cutter 3 to be pushed deeper into the bone. This could happen e.g. when the patient suffers from osteoporosis. The distance between the tip of the cutting edge 3c and the safety stop 4, and the relation between that distance and the length 31 of the guide channel 54, will determine the depth that the cartilage cutter 3 is allowed to go into the cartilage and/or bone. The safety stop 4 may be arranged such that that distance is adjustable.

In alternative exemplifying embodiments of the invention the surgical kit may comprise a cartilage cutting tool in form of a punch, to punch out the cartilage, or in form of a cartilage cut drill, to cut the cartilage and also cut/carve/drill the underlying bone, as are disclosed in PCT application PCT/EP2011/058473, see pages 17-18 and FIGS. 2, 5a-b and 10. The punch may for instance be advantageous when the implant 10 has a non-circular shape and/or the extending post 23 is not centrally placed in relation to the implant body 27.

In one embodiment the guide tool (1) according to the invention may be used together with a drill no, for drilling a cavity of the extending post, see FIG. 8b, and/or may be used together with a drill in for drilling the cavity of the implant body 27, see FIG. 8a.

Drill and Bone Remover

Figure 15:
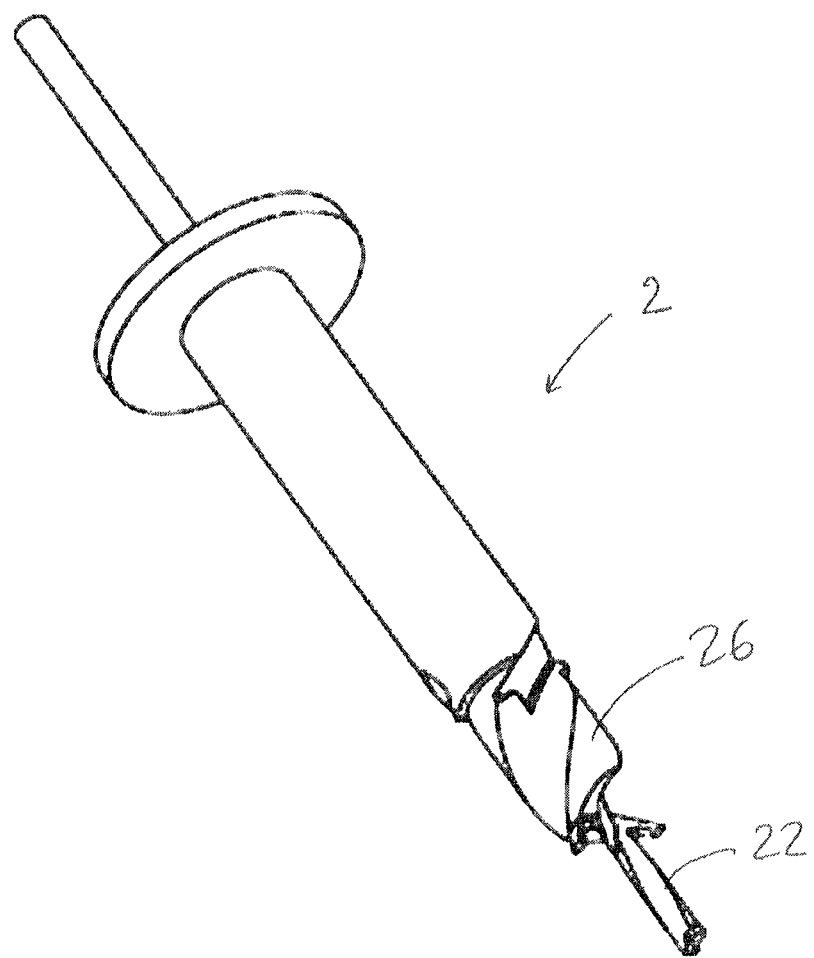
FIG. 15 shows another exemplifying embodiment of a drill and bone remover according to the present invention.

In one embodiment of the present invention the surgical kit comprises a drill and bone remover 2 (see FIGS. 2 and 10 and 15) that is used to drill a hole in the bone at the site of cartilage damage, for fastening of the extending post 23 of the implant 10 in the bone tissue, and simultaneously create a recess in the bone tissue at the site where the implant body 27 is to be received. The drill and bone remover 2 comprises a drill and bone remover body 20, a central drill 22 and a bone remover 26 part, as shown in FIG. 10 or 15. The central drill 22 extends from the center of the drill and bone remover body 20, i.e. corresponding to the position of a centrally placed extending post 23 on an implant 10 having a circular implant body 27. The diameter of the central drill 22 is the same as, or slightly smaller than, the diameter of the extending post 23 of the implant 10 that is to be implanted. The bone remover 26 has a cutting edge that is placed peripherally around the central drill 22. The diameter of the bone remover 26 is the same as, or slightly smaller than, the diameter of the implant body 27 of the implant 10 that is to be implanted, thus creating a recess that matches the implant body, in which the implant body can be received. The cutting edge of the bone remover 26 is hard enough for cutting or carving bone. It may be made of materials such as stainless steel.

The drill and bone remover body 20 is designed to fit the inside of the guide channel 54 of the guide body 13, with a slight tolerance to allow a sliding movement of the drill and bone remover 2 in the guide channel 54. In other words, the cross-sectional profile of the drill and bone remover body 20 matches the cross-sectional profile of the guide channel 54 as well as the of the implant 10, see FIG. 13a-b. The fit ensures the correct, desired placement of the drill and bone remover 2 on the cartilage surface and thus ensures the precise direction and placement of the drill hole for the extending post 23, as well as the recess for the implant body 27, in the bone.

The drill and bone remover 2, see FIG. 15 or FIG. 2 is also equipped with a depth gauge 7. The depth gauge 7 of the drill and bone remover determines the depth of the created drill hole as well as the recess for the implant body 27. The depth gauge 7 has a cross-sectional profile that is larger than the cross sectional profile of the guide channel 54. The depth gauge 7 will, during the surgical procedure, rest against the top of the guide body 13 and/or height adjustment device 16, thus preventing the drill and bone remover 2 to drill/carve/cut deeper into the bone. The distance between the tip of the cutting edge of the cutter 2 and the depth gauge 7, and the relation between that distance and the length 31 of the guide channel 54, will determine the depth that the is allowed to go into the cartilage and/or bone. The depth gauge 7 may be arranged such that that distance is adjustable. In a more preferred embodiment the distance is fixed and instead the drill/cut/carve depth is adjusted by adjusting the length 31 through the height adjustment device 16.

Figure 14:
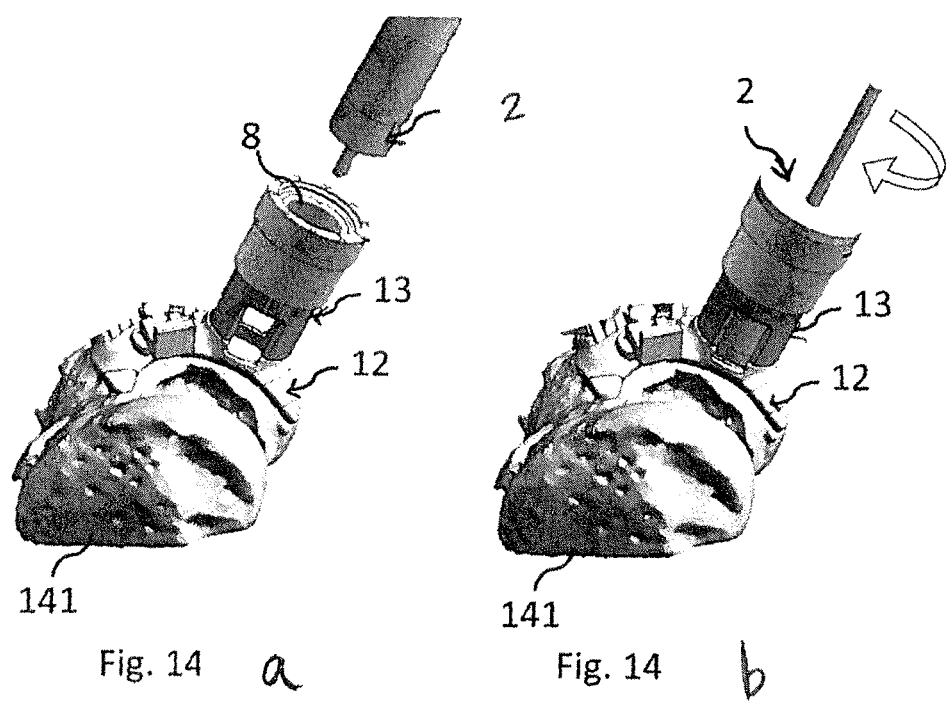
FIG. 14a-b shows an exemplifying embodiment of a method for implanting a cartilage implant using the guide tool of the present invention.

See FIG. 14a-b for a exemplified demonstration of how the drill and bone remover 2 may be used and how the drill depth is adjusted using the height adjustment device 16.

Another exemplified embodiment of the drill and bone remover or implant specific drill bit 2 according to the invention is shown in FIG. 15. In the exemplified embodiment of the drill and bone remover in FIG. 15, the bone remover 26 part further comprises flanges 28 which is designed to correspond to, at least a rotational volume of the bone remover part 26 corresponds to the shape of an implant comprising a protruding rim on the implant body 27. The rotational volume is a fictive volume achieved by the drill and bone remover when it is rotated around its longitudinal axis.

In alternative exemplifying embodiments of the invention the surgical kit may, instead of an integrated drill and bone remover, comprise a drill bit for drilling the hole for the extending post and a reamer for removing bone where the implant body is to be received in the bone. Such embodiments may also comprise a drill guide and/or a reamer guide. Examples have been disclosed in PCT application PCT/EP2011/058473, see pages 18-20 and 21 of the description and FIGS. 6-7. Such tools may for instance be used when the implant 10 has a non-circular shape and/or the extending post 23 is not centrally placed in relation to the implant body 27.

Implant Dummy

Figure 11:
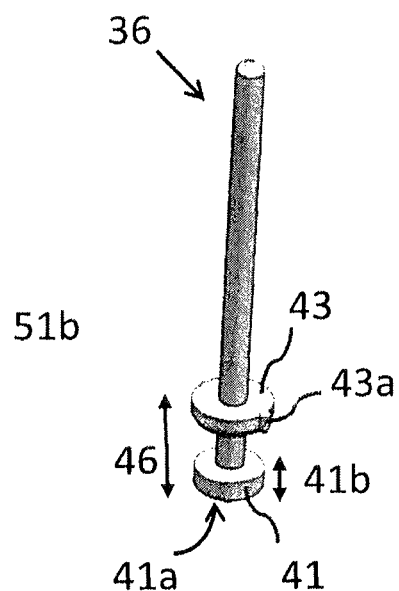
FIG. 11 show exemplifying embodiments of an implant dummy (b) according to the present invention.

The implant dummy 36 and dummy reference 37, see FIGS. 2 and 11, are used to make sure that the cut, carved or drilled recess in the bone that is to receive the implant body 27, is deep enough to fit the implant. This is very important, since the articulate surface 15 of the implant 10 must not project over the surface of the surrounding cartilage tissue. If it would it could cause a lot of damage to the surrounding cartilage and to the cartilage on the opposite side of the joint. Preferably the articulate surface 15 should form a continuous surface with the surrounding cartilage, neither projecting above nor being sunken below the surface of the surrounding cartilage. The checking of the recess depth is difficult or impossible to do with the implant 10 itself, since the implant 10, e.g. with its extending post 23, is designed to be fixed in the bone once inserted, and thus is difficult or impossible to remove. The implant dummy, on the other hand, is designed for easy removal from the recess once the recess depth has been checked.

The implant dummy 36, see FIG. 11, has an implant element 41 that is designed to match the implant body 27. The lower surface 41a of the implant element 41 is a replica of the bone contact surface 21 of the implant that is to be implanted. That is, if the implant 10 and bone contact surface 21 is custom made for the specific patient, the implant element 41 and its lower surface 41a will also be custom made and the lower surface 41a be a replica of the bone contact surface 21. The cross-sectional profile of the implant element 41 corresponds to the cross-sectional surface 82 of the implant body, or is slightly smaller in order to ensure easy removal of the implant dummy from the recess.

The implant dummy 36 also has a top surface 43. The distance 46 between the lower surface 41a of the implant element 41 and the top surface 43 corresponds to the distance that you get when adding the thickness or height 14 of the implant body 27 (corresponding to the depth of the recess in the bone plus the thickness of the corresponding cartilage), the height of the guide hole 53 and/or the length 51a of the dummy reference 37, taking regard to any overlap between the guide hole 53 and the dummy reference 37 when they are attached. For a demonstration on how the recess depth is checked using the implant dummy 36 together with the dummy reference 37, see below in connection with FIGS. 14a-b?. In one embodiment the thickness 41b of the implant element 41 is the same as the thickness 14 of the implant body 10, such that the recess depth can also be checked directly using the implant element 41 only, i.e. without the dummy reference 37 and top surface 43.

Mandrel

The mandrel 35 (see FIGS. 2 and 12) consists of a solid body and has a mandrel surface 35a that is designed to fit the articulate surface 15 of the implant 10, i.e. it has a corresponding cross-sectional profile and preferably also a corresponding, although inverted, curvature. The mandrel may also be designed to fit the inside of the guide channel 54, with a slight tolerance to allow a sliding movement of the hammer tool 35 in the guide channel 54. The mandrel 35 is preferably used inside the guide channel 54 to hammer the implant in place, for support and to get the proper angle, or may alternatively be used without the support from the guide channel 54, see FIG. 2. The height 68 of the mandrel 35 is in one embodiment the same height 31 as of the guide channel 54. For such embodiment, once the mandrel 35 is hammered in the same level as the top of the guide channel, the hammering and thus the placement of the implant is finished.

Figure 12:
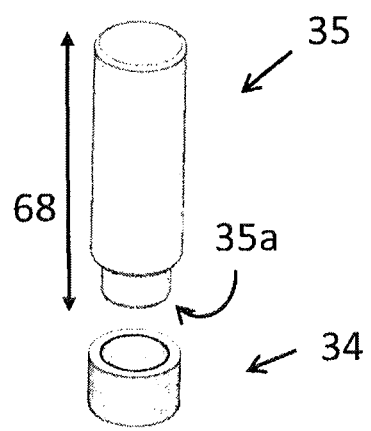
FIG. 12 shows an exemplifying embodiment of a mandrel according to the present invention.

The hammer tool 35 may also be accompanied by a hammer tool adapter 34, see FIG. 12, for facilitating the use of the hammer tool and minimizing the absorption of the shock caused by the hammer tool and/or minimize the risk of scratching the surface of the implant 10 while hammering. It is made from a soft material that is gentle to the implant surface, e.g. a rubber or plastic material.

Design Method for Designing a Guide Tool, Kits of Tools and Medical Implant, a Grafted Plug or an Artificial Plug The design method describing the design of the guide tool (1) and set of insert tools and the implant disclosed herein will now be further explained.

A design method according the present invention may be generating the cross-section profile 82, 122 for a guide channel 54 in a guide body 13 extending from the positioning body 11 further comprising a female receiving part 48 and a male part 47 of a height adjustment device 16, said guide channel 54 extending through out said positioning body 11 and said guide body 13 and said male part 47, wherein said mail part 47 is placed inside the female receiving part 48.

Further the design method involves designing the female receiving part 48 to comprise grooves or ledges 17 at different heights relative to the cartilage contact surface 50 of the guide tool. The male part 47 designed to comprise a guide channel 54 inside the male part 47, the guide channel 54 may be designed as cylinder shaped and further the male part 47 is further designed to have protruding ridges 105 on the outer surface of the male part 47. When the male part 47 is placed inside the female receiving part 48 the protruding ridges 105 of the male part 47 is placed or located inside one of the grooves 17 on the female receiving part 48. The position of the grooves 17 and the position of the ridges 105 in relation to the positioning body or the cartilage contact surface 50 may be used to adjust or regulate the length 31 of the guide body 13 due to the design of the guide tool (1) according to the present invention.

The method of designing a guide tool (1) comprising a height adjustment device for cartilage repair in an articulating surface of a joint according to the invention comprising for example the steps of:

I. Determining physical parameters for cartilage damage in a joint, comprising:
  a. obtaining image data representing a three dimensional image of a bone member of the joint;
  b. identifying in the image data of cartilage damage in an articulate surface of the bone member;
  c. determining based on the image data the location of the cartilage damage;
  d. determining based on the image data the size and shape of a cartilage damage;
  e. determining based on the image data the surface contour curvature of the cartilage and/or the subchondral bone in the joint in a predetermined area comprising and surrounding the site of cartilage damage;

II. Generating design parameters for a medical implant 10, a grafted plug 600 or an artificial plug, comprising:
  a. generating the contour curvature for an articulate surface of an implant body 27, 627 dependent on said determined surface curvature of the cartilage and/or the subchondral bone;
  b. generating a cross-section for the implant body dependent on and substantially corresponding to said determined size and shape of the damaged cartilage or corresponding or generating a cross-section for the implant body 27, 627 together with another cross-section for another other implant 10 or grafted plug 60o or an artificial plug to said determined size and shape of the damaged cartilage by forming a pattern;
  c. generating an edge height 14, 710 for the implant body 27, 627 that substantially corresponds to the thickness of healthy cartilage plus a selected height of a bone contacting part of the implant for countersinking the implant 10, a grafted plug 600 or an artificial plug into a recess to be made in the bone to fit and receive the implant 10, the grafted plug 600 or the artificial plug;

III. Generating design parameters of a guide tool (1) for implanting said implant 10 or, a grafted plug 600 or an artificial plug comprising:
  a. generating the contour curvature for a cartilage contact surface 50 of a positioning body if dependent on said determined surface contour curvature of the cartilage and/or the subchondral bone in the joint in a predetermined area comprising and surrounding the site of cartilage damage, such that said cartilage contact surface 50 of the positioning body if corresponds to and fits to said surface contour of the cartilage or the subchondral bone in the joint;
  b. generating the cross-section profile 82, 122 for a guide channel 54 in a guide body 13 further comprising a female receiving part 48 of a height adjustment device 16 extending from the positioning body ii, said guide channel 54 passing through said positioning body 11, and said guide body 13 and said male part 47 placed inside the female receiving part 48, the cross-section profile 82, 122 for the guide channel 54 being generated dependent on and substantially corresponding to said determined size and shape of the damaged cartilage, and such that the guide channel 54 is designed to have a cross-sectional profile 82, 122 that corresponds to the cross-section 81, 121 the implant body 27, 627 or that corresponds to the combination of at least two cross-sections 81, 121 of the implant body 27, 627, and such that the guide channel 54 is designed to have a muzzle 29 on the cartilage contact surface 50 of the positioning body 11 at a position corresponding to the site of the diseased cartilage;
  c. generating the shape of the guide body 13 of guide tool, depending on the design of the positioning body 11 and wherein the guide body 13 is designed to be attached to the positioning body 11;
  d. generating shape of the height adjustment device 16 wherein the female receiving part 48 of the guide body 13 is designed to comprise grooves 17 and the male part designed to fit inside the female receiving part 48 is designed to comprise ridges 105 which is designed to fit in the grooves of the female receiving part and wherein the male part 47 may be turned so that the ridge 105 may fit in different grooves 17 in the female receiving part 48 and wherein the different positions gives different heights 31 of the guide channel 54 which may be used to adjust for controlling drill depths.
  e. generating the cross-section profile 84, 124 for an insert tool to have a cross-sectional profile that corresponds to the cross-sectional profile 82 of the guide channel 54 with a tolerance enabling the insert tool to slide within the guide channel 54.

The design method above wherein the order of the said steps k. and l. may be in any order, for example first k. then l. or first l. then k.

The design method according to the invention wherein the guide body 13 is a standard component and the positioning body 11 is component which is individually designed to fit a persons joint and wherein the guide body 13 and the positioning body 11 are designed to fit to each other.

Detailed Description of a Method for Implanting the Implant Using the Set of Tools Use of the guide tool (1) and set of tools disclosed herein will now be further explained in connection with an exemplifying embodiment partly shown in FIGS. 14a-b. The example concerns a guide tool (1) comprising a height adjustment device 16 for implantation of a small implant 10 into a joint. The same principles do however apply also for other joints as well as for mosaicplasty surgery. For the latter a guide body 13 with more than one guide channel 54 may be used, and the grafted plug 600 may be a selection of bone and cartilage plugs from a healthy part of the joint, or a selection of artificial implant plugs of various sizes.

Figure 1:
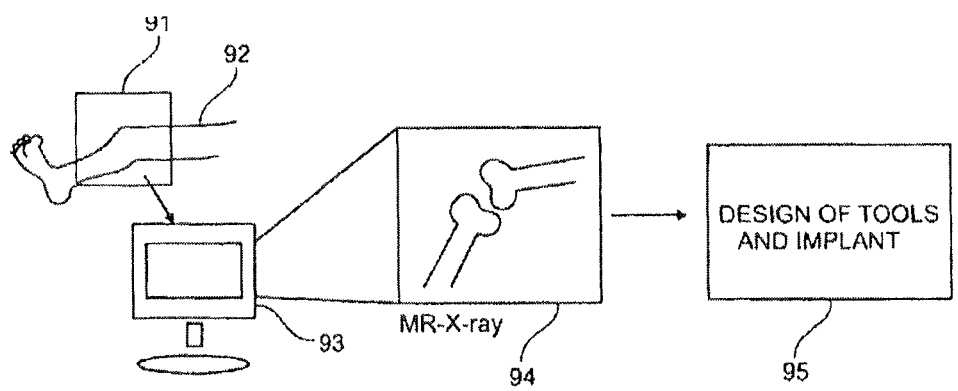
FIG. 1 shows a schematic overview of an exemplifying method used for designing a patient specific surgical tool, for example a guide tool.

1. Localize the area of the injury and determine the desired size and shape of the implant, see FIG. 1. The position and size of the cartilage damage can be identified by a combination of MRI or CT images or by dGEMRIC technique. The images may then be handled in special surgical planning tool software. All of the parts in the surgical kit may be individual adjusted depending on size of cartilage damage, location of the cartilage damage and also depending on a simulation of the individual surface appearance without damage. Alternatively an implant from a set of predetermined implants may be selected and the set of tools designed or selected thereafter.

2. The implant 10 and set of tools of the invention are manufactured depending on; the size of the implant needed, the localization of the injury, the appearance of the cartilage surface intended to be replaced. The designs may be based on the MR images/CT-scanning images from the joint of the person having the cartilage damage, using the surgical planning software. The surgical planning software is connected to manufacturing devices, for example a laser printer, a lathe and/or a reamer, and the parts of the kit are manufactured using e.g. additive manufacturing, laser sintering techniques, turnery or reaming.

3. A surgical opening is made in the leg tissue depending on the localization of the injury and the size of the implant and also depending on the size and conformation of the guide tool.

4. The guide base 12 is placed on the surface of the knee cartilage, see FIG. 2 for an exemplified embodiment of the guide tool (1) intended to use in a knee joint. The guide base 12 fits due to the fact that it is custom made to be placed in that particular position. This allows the surgical procedure (cartilage and bone removal and insertion of the implant) to be performed with good accuracy and precision. If necessary the guide tool (1) can be further stabilized with rivets or pins on a part of the guide tool (1) that is in contact with parts of the joint that have no cartilage tissue.

5. The guide body 13 is attached to the guide base 12. The guide body 13 is further be provided with a height adjustment device 16 comprising a guide channel 54 of the right shape and size, i.e having a cross-sectional profile that corresponds to the cross-sectional profile 81 of the implant that is to be implanted.

6. The guide tool (1) is used to drill a recess for the implant to be implanted. In alternative embodiments a drill and bone remover 2 is used which both drills for the extending post and for the implant body using the same instrument (see FIG. 2 or 15).

9. An implant dummy 36 may be used to check whether the recess in the bone is deep enough to receive the implant 10, without the implant 10 projecting over the surface of the surrounding cartilage. This can be ensured by using the height adjustment device 16 and adjust the drill depth.

The height adjustment device 16 is used to adjust the length 31 of the guide channel 54, by moving one protruding ridge 105 from one groove 17 to another groove 17 with a shorter distance to the cartilage contact surface compared to the first groove. This shortening of the length 31 of the guide channel 54 may be performed at a number of preset intervals, e.g. one, two or three times 200 μm, or any other number times any other preset interval, see also above, see for example FIG. 7a-c wherein the male part 47 is placed in different positions inside the female receiving part 48 of the height adjustment device 16 thereby achieving different lengths 31 of the guide channel 54. This adjustment in small step makes the implantation procedure to be more precise.

The drilling and cutting procedure is then repeated; and the implant dummy 36 may be used to check the drill depth again 10. The implant 10 may be guided to the exact matching recess at the site of implantation through the guide channel 54 of the guide body 13, or alternatively be placed at the site of implantation without the guide.

11. The mandrel 35, see FIG. 2, is then used, also either with or without support from the guide channel 54 of the guide body 13, to hammer the implant in position and firmly attach it to the bone. The mandrel 35 is placed on top of the implant 10 and then a hammer or similar tool is used to hammer or push the mandrel such that the implant is forced in place, 12. Lastly, the hammer tool 35 and the guide base 12 are removed, the implant 10 is implanted at the site of cartilage damage. This is an exemplified embodiment of use of the guide tool (1) according to the invention.

The invention claimed is:

1. A guide tool adapted for removal of damaged cartilage and bone and adapted for guiding insert tools during repair of diseased cartilage at an articulating surface of a joint, wherein the guide tool comprises:
   a guide base having a positioning body and a guide body protruding from the guide base, wherein the guide body comprises: a height adjustment device including: a female receiving part comprising an inner surface provided with a plurality of grooves extending from an edge of an upper opening of the female receiving part, wherein each groove of the plurality of grooves is separate from an adjacent groove of the plurality of grooves along an entire groove length, wherein the entire groove length of each groove of the plurality of grooves is different; and
   a male part equipped with at least one ridge that protrudes from an outer surface of the male part; and
   a guide channel with a length, the guide channel extending throughout the guide body and through the height adjustment device with one opening at a cartilage contact surface of the positioning body and another opening at a top of the height adjustment device, and
   wherein the height adjustment device is arranged to enable stepwise adjustment of the length of the guide channel.

2. The guide tool according to claim 1, wherein the guide body, the female receiving part, and the male part comprises the guide channel, wherein the other opening of the guide channel is at a top of the male part of the height adjustment device, and wherein the length of the guide channel is adjusted by moving the male part in relation to the female receiving part so that the at least one ridge of the male part is moved from one groove of the plurality of grooves to another groove of the plurality of grooves.

3. The guide tool according to claim 2, wherein the at least one ridge of the male part is moved from one groove of the plurality of grooves to another groove of the plurality of grooves by lifting the male part outwards from the female receiving part to remove the at least one ridge from the one groove and then placing the at least one ridge of the male part down in the other groove, and wherein the male part when placed inside the female part is in a locked position and is not able to rotate due to placement of the at least one ridge in the other groove.

4. The guide tool according to claim 1, wherein the stepwise height adjustment is made by steps of 0.01-0.4 mm due to a position of a groove of the plurality of grooves relative to the cartilage contact surface.

5. The guide tool according to claim 1, wherein the guide channel has a cross-sectional profile that is designed to correspond to a cross-sectional profile of an implant body.

6. The guide tool according to claim 1, wherein the cartilage contact surface is designed to fit a contour of cartilage or subchondral bone of an average patient or of a specific patient.

7. The guide tool according to claim 1, wherein the positioning body is arranged with at least one breakage means for enabling easy removal of part of the positioning body by tearing, fracturing, or breakage, the breakage means being provided by grooves, slots, of perforations, or other weakening of the breakage means.

8. The guide tool according to claim 1, wherein the guide tool is also adapted for insertion of a medical implant, a grafted plug or an artificial plug having an implant body with a predetermined cross-sectional profile.

9. The guide tool according to claim 1, wherein the male part when placed inside the female part is in a locked position and is not able to rotate due to placement of the at least one ridge of the male part in a groove of the plurality of grooves of the female receiving part.

10. The guide tool according to claim 1, wherein the plurality of grooves extending from the edge of the upper opening of the female receiving part have a cross-section allowing the at least one ridge to enter a groove of the plurality of grooves of the female receiving part and stop against an abutment of the groove.

11. The guide tool according to claim 1, wherein the male part has a cross-sectional profile that corresponds to a cross-sectional profile of a female part guide channel with a tolerance enabling an insert tool to slide within the female part guide channel.

* * * * *